United States Patent
Jun et al.

(10) Patent No.: US 9,920,105 B2
(45) Date of Patent: Mar. 20, 2018

(54) HUMAN FERRITIN-DERIVED FUSION POLYPEPTIDE

(71) Applicant: Kyungpook National University Industry-Academic Cooperation Foundation, Daegu (KR)

(72) Inventors: Eunsung Jun, Daegu (KR); Jaeog Jeon, Daegu (KR); Soyoun Kim, Daegu (KR); In-Seop So, Daegu (KR); In-San Kim, Daegu (KR); Sun-Ji Kim, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 5 days.

(21) Appl. No.: 14/820,865

(22) Filed: Aug. 7, 2015

(65) Prior Publication Data
US 2016/0060307 A1    Mar. 3, 2016

Related U.S. Application Data

(63) Continuation of application No. PCT/KR2014/001094, filed on Feb. 10, 2014.

(30) Foreign Application Priority Data

Feb. 8, 2013    (KR) .................. 10-2013-0014510

(51) Int. Cl.
*A61K 38/00* (2006.01)
*C07K 14/47* (2006.01)

(52) U.S. Cl.
CPC .......... *C07K 14/47* (2013.01); *C07K 2319/00* (2013.01); *C07K 2319/20* (2013.01)

(58) Field of Classification Search
None
See application file for complete search history.

(56) References Cited

U.S. PATENT DOCUMENTS 8,017,729 B2    9/2011    Shiba et al.
8,975,369 B2    3/2015    Cha et al.

FOREIGN PATENT DOCUMENTS

| KR | 10-2007-0089236 | 8/2007 |
| KR | 10-2012-0118186 | 10/2012 |
| WO | 01/98245 | 12/2001 |

OTHER PUBLICATIONS

Kramer et al., J. Am. Chem. Soc., 2004, 126(41), 13282-86.*
Hong et al., J. Cell Mol. Med., 2008, 12(5B), 2003-14.*
Li et al. Cellular and Molecular Immunology, vol. 6, No. 6, Dec. 2009.*
Nelms, et al., "The IL-4 Receptor: Signaling Mechanisms and Biologic Functions", Annual Review of Immunology, 1999, p. 701-738, vol. 17.
Paul, William, "Interleukin-4: A Prototypic Immunoregulatory Lymphokine", Blood, May 1, 1991, p. 1859-1870, vol. 77, No. 9.
Lee, et al., "IL-4-induced Oxidative Stress Upregulates VCAM-1 Gene Expression in Human Endothelial Cells", Journal of Molecular and Cellular Cardiology, 2001, p. 83-94, vol. 33.
Sasaguri, et al., "A role for interleukin 4 in production of matrix metalloproteinase 1 by human aortic smooth muscle cells", Atherosclerosis, 1998, p. 247-253, vol. 138.
Davenport, et al., "The Role of Interleukin-4 and Interleukin-12 in the Progression of Atherosclerosis in Apolipoprotein E-Deficient Mice", American Journal of Pathology, Sep. 2003, p. 1117-1125, vol. 163, No. 3.
King, et al., "Interleukin-4 Deficiency Decreases Atherosclerotic Lesion Formation in a Site-Specific Manner in Female LDL Receptor -/- Mice", Arteriosclerosis, Thrombosis, and Vascular Biology, 2002, p. 456-461, vol. 22.
Shurin, et al., "Th1/Th2 balance in cancer, transplantation and pregnancy", Springer Seminars in Immunopathology, 1999, p. 339-359, vol. 21.
Dancescu, et al., "Interleukin 4 Protects Chronic Lymphocytic leukemic B Cells from Death by Apoptosis and Upregulates Bcl-2 Expression", The Journal of experimental medicine, Nov. 1992, p. 1319-1326, vol. 176.
Todaro, et al., "Apoptosis resistance in epithelial tumors is mediated by tumor-cell-derived interleukin-4", Cell Death and Differentiation, 2008, p. 762-772, vol. 15.
Todaro, et al., "Colon Cancer Stem Cells Dictate Tumor Growth and Resist Cell Death by Production of Interleukin-4", Cell Stem Cell, Oct. 2007, p. 389-402, vol. 1.
Joshi, et al., "In Situ Expression of Interleukin-4 (IL-4)Receptors in Human Brain Tumors and Cytotoxicity of a Recombinant IL-4 Cytotoxin in Primary Glioblastoma Cell Cultures", Cancer Research, Nov. 15, 2001, p. 8058-8061, vol. 61.
Garland, et al., "Phase I Trial of Intravenous IL-4 Pseudomonas Exotoxin Protein (NBI-3001) in Patients with Advanced Solid Tumors That Express the IL-4 Receptor", Journal of Immunotherapy, Jul./Aug. 2005, vol. 28, No. 4.
Kioi, et al., "Expression and Targeting of Interleukin-4 Receptor for Primary and Advanced Ovarian Cancer Therapy", Cancer Research, Sep. 15, 2005, vol. 65, No. 18.
Kawakami, et al., "Interleukin 4 Receptor on Human Lung Cancer: A Molecular Target for Cytotoxin Therapy", Clinical Cancer Research, Nov. 2002, p. 3503-3511, vol. 8.
Andrews, et al., "IL-4 Receptor α Is an Important Modulator of IL-4 and IL-13 Receptor Binding: Implications for the Development of T herapeutic Targets", Journal of Immunology, 2006, p. 7456-7461, vol. 176.
Corry, et al., "Interleukin 4, but Not Interleukin 5 or Eosinophils, Is Required in a Murine Model of Acute Airway Hyperreactivity", Journal of Experimental Medicine, Jan. 1996, p. 109-117, vol. 183.
Lee, et al., "Differential requirement for CD18 in T-helper effector homing", Nature Medicine, Oct. 2003, p. 1281-1286, vol. 9, No. 10.
Lee, et al., "Airway glycoprotein secretion parallels production and predicts airway obstruction in pulmonary allergy", Journal of allergy and clinical immunology, Jan. 2004, p. 72-78, vol. 113, No. 1.

(Continued)

*Primary Examiner* — Jeanette Lieb
(74) *Attorney, Agent, or Firm* — H.C. Park & Associates, PLC

(57) ABSTRACT

A fusion polypeptide, including a first polypeptide fragment including 5 to 30 amino acids, the first polypetide fragment is fused between a first amino acid and a fifth amino acid of a fourth loop of a human-derived ferritin monomer.

26 Claims, 18 Drawing Sheets

(56) References Cited

OTHER PUBLICATIONS

Kramer, et al., "Engineered Protein Cages for Nanomaterial Synthesis", Journal of the American Chemical Society, 2004, p. 13282-13286, vol. 126, No. 41.

Hong, et al., "Phage display selection of peptides that home to atherosclerotic plaques: IL-4 receptor as a candidate target in atherosclerosis", Journal of cellular and molecular medicine, 2008, p. 2003-2014, vol. 12, No. 5B.

Wu, et al., "Tumor-Targeting Peptide Conjugated pH-Responsive Micelles as a Potential Drug Carrier for Cancer Therapy", Bioconjugate Chemistry, 2010, p. 208-213, vol. 21, No. 2.

Gollan, et al., "Redirecting Retroviral Tropism by Insertion of Short, Nondisruptive Peptide Ligands into Envelope", Journal of Virology, Apr. 2002, p. 3558-3563, vol. 76, No. 7.

Hart, et al. "Cell Binding and Internalization by Filamentous Phage Displaying a Cyclic Arg-Gly-Asp-containing Peptide", Journal of Biological Chemistry, Apr. 29, 1994, p. 12468-12474, vol. 269, No. 17.

International Search Report dated Jun. 20, 2014, in International Patent Application No. PCT/KR2014/001094.

Written Opinion of the International Search Authority dated Jun. 20, 2014, in International Patent Application No. PCT/KR2014/001094.

\* cited by examiner

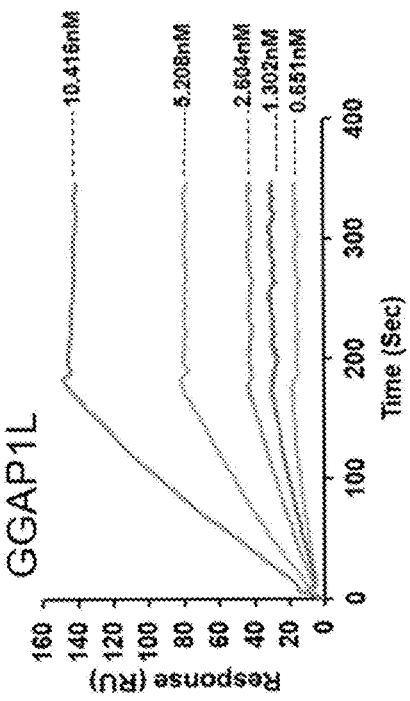
FIG. 9A
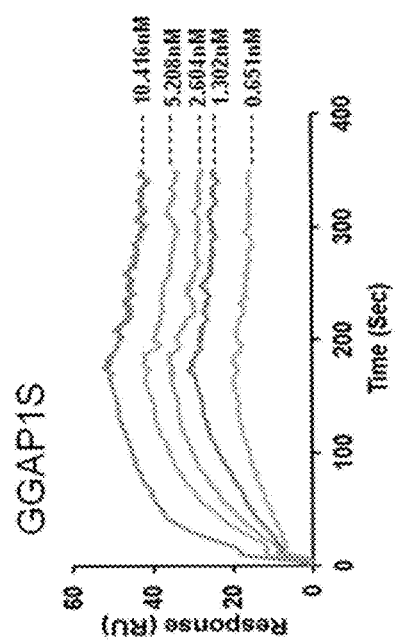
FIG. 9B
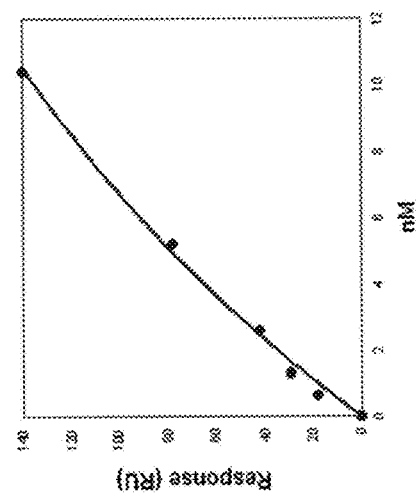
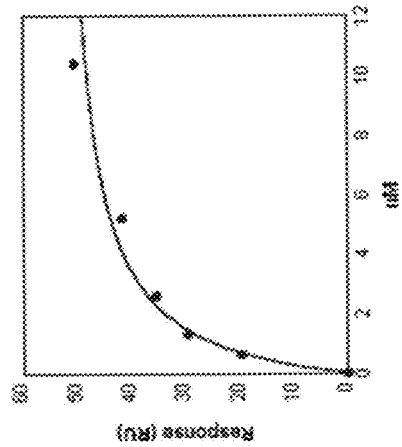

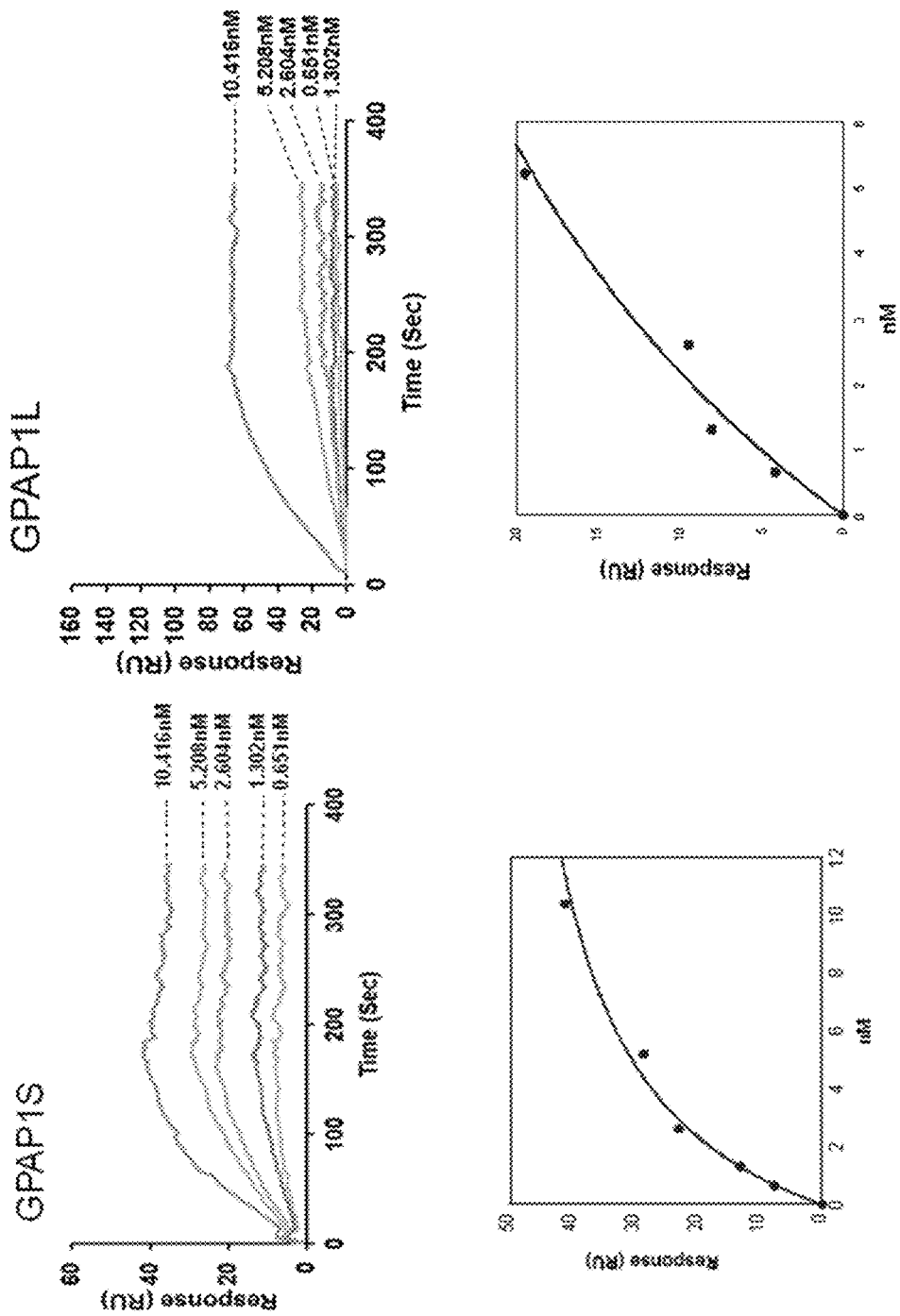

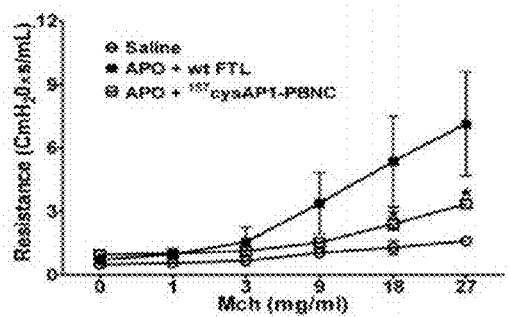
FIG. 17A
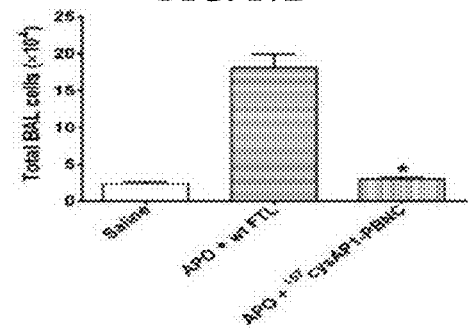
FIG. 17B
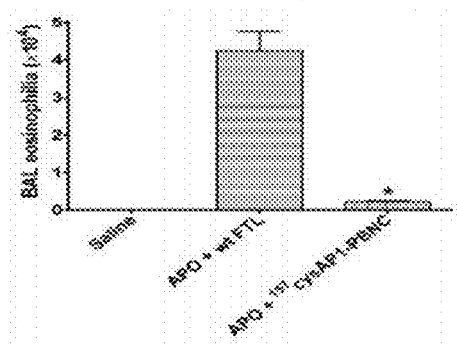
FIG. 17C
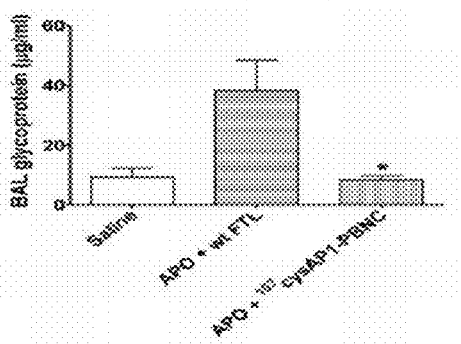
FIG. 17D
FIG. 17E
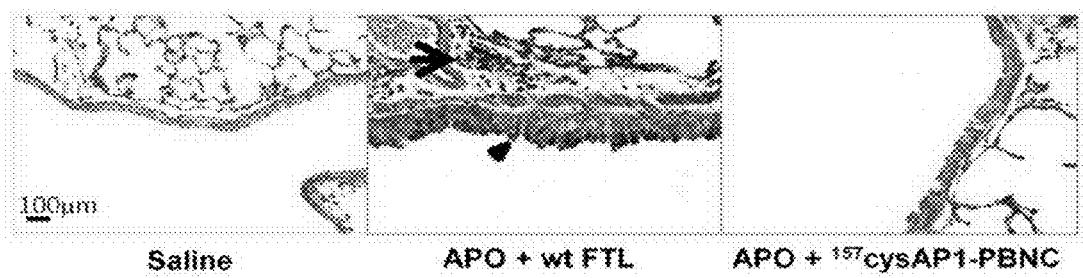

HUMAN FERRITIN-DERIVED FUSION POLYPEPTIDE

CROSS-REFERENCE TO RELATED APPLICATIONS

The present application is a continuation of International Patent Application No. PCT/KR2014/001094, filed on Feb. 8, 2014, which claims priority from Korean Patent Application No. 10-2013-0014510 filed on Feb. 8, 2013. The present application claims priority to both applications and both disclosures are hereby incorporated by reference in their entirety.

FIELD

Exemplary embodiments relate to a fusion polypeptide. More specifically, exemplary embodiments relate to a fusion polypeptide in which a polypeptide fragment including 5 to 30 amino acids is fused between the first amino acid and the fifth amino acid of the fourth loop of a human-derived ferritin monomer.

SEQUENCE LISTING

This application is being filed electronically via the USPTO EFS-WEB server, as authorized and set forth in MPEP §502.05 and this electronic filing includes an electronically submitted sequence listin. The entire content of this sequence listing is hereby incorporated by reference into the specification of this application. The sequence listing is identified on the electronically filed ASII (.txt) text file as follows:

| File Name | Date of Creation | Size |
|---|---|---|
| OP15-0062.txt | Aug. 7, 2015 | 27.41 kilobytes |

DISCUSSION OF THE BACKGROUND

Cage proteins form macromolecules. Macromolecules have molecular weights that are tens to hundreds of times larger than those of low-molecular weight monomers due to a precise self-assembly property of monomers. Viral capsid proteins, ferritins, heat shock proteins, and DNA-binding proteins from strayed cells (Dps proteins) are classified as cage proteins. While cage proteins are hollow inside, each monomer constituting a cage protein has a very regular and precise interaction with adjacent monomers. Since the inside of the cage protein is isolated from the outside of the cage protein (due to the nature of the container-like property of the cage protein) the cage protein is frequently used as a drug delivery system in the medical field.

Researches are actively researching viral vectors and non-viral vectors in the cage protein-applied material transport field. Currently, adenovirus is often studied as a viral vectors and ferritins and heat shock proteins are studied as non-viral vectors. However, the conventional viral vectors have been reported to cause in vivo safety problems due to the genes of the viruses.

Ferritin is a kind of intracellular protein, while functioning to store and release iron. Ferritin is generally in the form of a hollow spherical cage in vivo. The cage is composed of 24 subunits. The subunits are divided into heavy chains and light chains depending on their structures.

Although human-derived ferritin protein does not have the safety problems involved with viral vectors, human-derived ferritin protein mave have diminished specific binding affinity where a targeting moiety binds to a certain region. In some cases, the human-derived ferritin protein does not form a cage. Therefore, there is an urgent need to develop fusion polypeptides that can be effectively delivered to a target by enhancing specific affinity of a targeting moiety that may effectively form a cage (i.e., have no problems in the formation of a cage).

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a fusion polypeptide that is prepared with a polypeptide fragment that binds to the targeting molecules, cells, and/or tissues very effectively as well as favorably forms a protein cage. Exemplary embodiments include methods as well as an agent, a pharmaceutical composition, a drug delivery system, a protein cage, an expression vector, a polynucleotide, a ferritin protein that includes the fusion polypeptide, Additional aspects will be set forth in part and in the description which follows and, in part, will be apparent from the disclosure, or may be learned by practice of the inventive concept.

An exemplary embodiment discloses an agent including a fusion polypeptide that includes an amino acid sequence selected from the group consisting of SEQ ID NOs: 2-5, 23, 25, 27, 29, and 31. The fusion polypeptide is an active ingredient for treating asthma.

BRIEF DESCRIPTION OF THE DRAWINGS

FIG. 9A is a surface plasmon resonance analysis result measuring binding affinity of AP1 peptide-inserted ferritins to IL-4 receptor (GGAP1S) for ferritins having AP1S inserted in a GG cassette.

FIG. 9B is a surface plasmon resonance analysis result measuring binding affinity of AP1 peptide-inserted ferritins to IL-4 receptor (GGAP1L) for ferritins having AP inserted in a GG cassette.

FIG. 9C is a surface plasmon resonance analysis result measuring binding affinity of AP1 peptide-inserted ferritins to IL-4 receptor (GPAP1S) for ferritin having AP1S inserted in a GP cassette.

FIG. 9D is a surface plasmon resonance analysis result measuring binding affinity of AP1 peptide-inserted ferritins to IL-4 receptor (GPAP1L) for ferritin having AP inserted in a GP cassette.

FIGS. 17A through 17E show animal test results confirming that asthma symptoms were mitigated by AP1 peptide-inserted ferritin cages ($^{157}$cysAP1-PBNC) (Data are indicated as the mean and standard error of the mean (SEM) of results through three independent tests. "*" indicates a significant change (p<0.05) compared with APO+wt FTL. Saline: group treated with saline, APO+wtFTL: group administered with wild type ferritin cage without AP1 after asthma induction, APO+157cysAP1-PBNC: group administered with AP1-containing ferritin cage after asthma induction).

FIG. 17A is a graph that shows measurement results of air hyper-responsiveness (AHR) using a FlexiVent system after asthma was induced by *A. oryzae* protease (APO) mixed with OVA, as an allergen.

FIG. 17B is a graph that shows measurement results of bronchoalveolar lavage (BAL) cell count.

FIG. 17C is a graph that shows measurement results of BAL eosinophils cell count.

FIG. 17D is a graph that shows measurement results of glycoprotein secretion amount in BAL fluid.

FIG. 17E are images that show observation results of lung tissues of mice to be tested.

DETAILED DESCRIPTION OF THE ILLUSTRATED EMBODIMENTS

Figure 1:
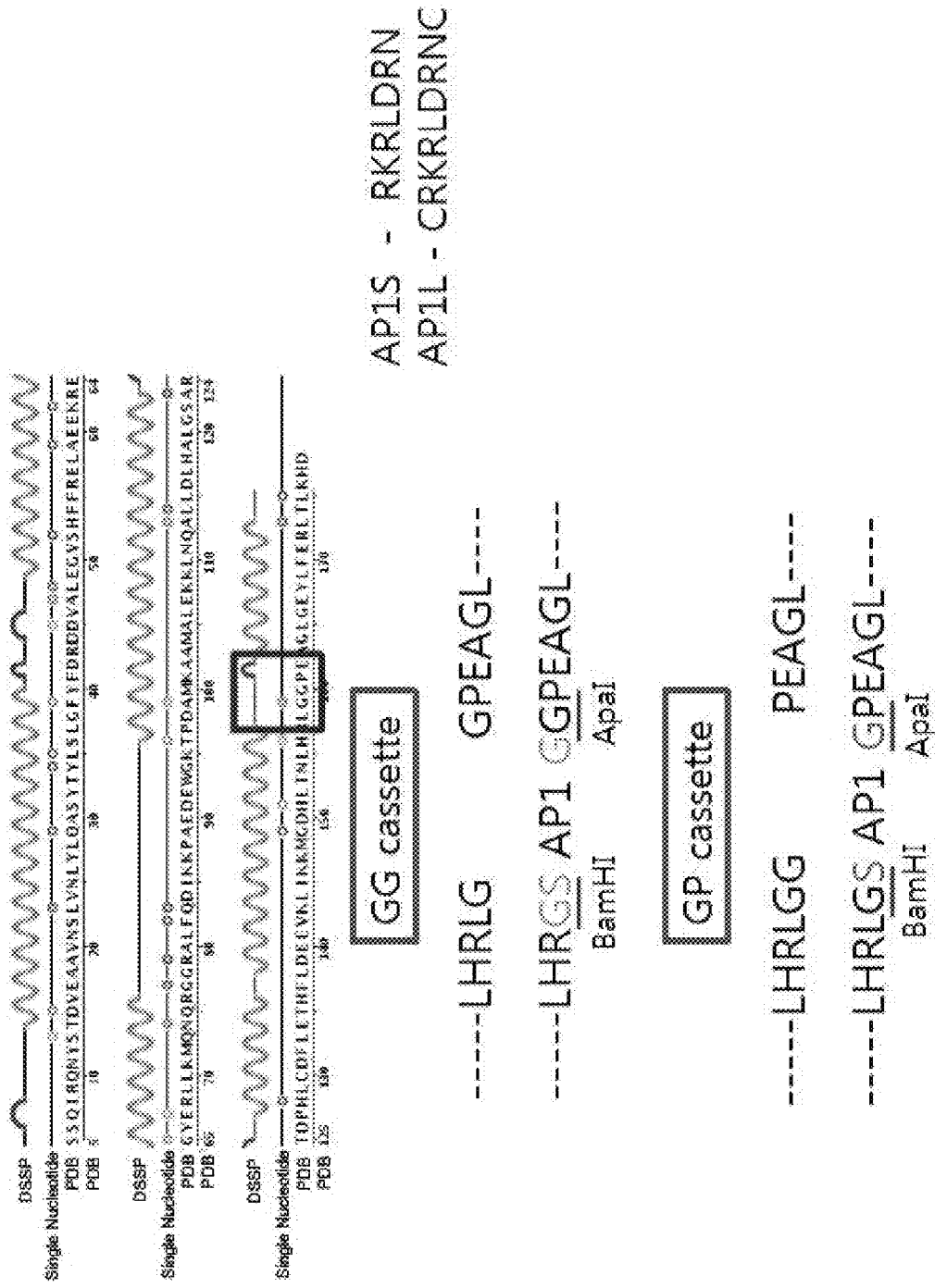
FIG. 1 is a schematic view in which an AP1 peptide is introduced in the fourth loop of the human ferritin light chain (AP1 in GG cassette or GP cassette: AP1S or AP1L sequence).
Figure 2A:
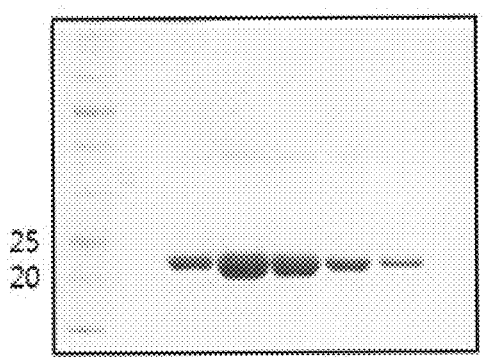
FIG. 2A is an image of electrophoresis results of an AP1 peptide-inserted fusion protein after purification where a ferritin having AP1S is inserted in a GG cassette.
Figure 2B:
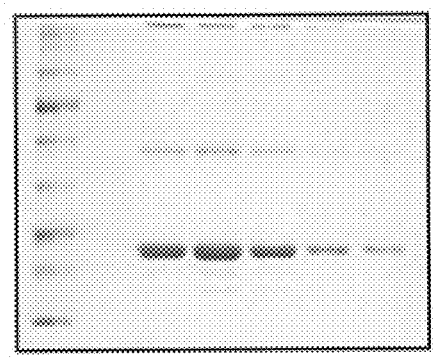
FIG. 2B is an image of electrophoresis results of an AP1 peptide-inserted fusion protein after purification where a ferritin having AP is inserted in a GG cassette.
Figure 2C:
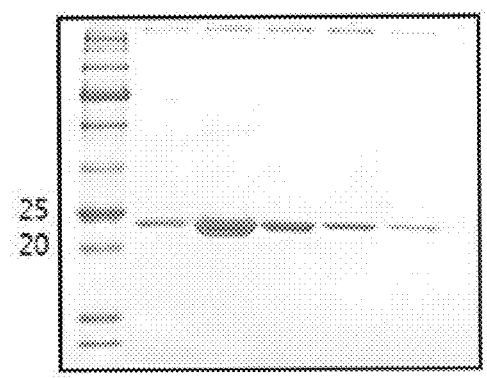
FIG. 2C is an image of electrophoresis results of an AP1 peptide-inserted fusion protein after purification where a ferritin having AP1S is inserted in a GP cassette.
Figure 2D:
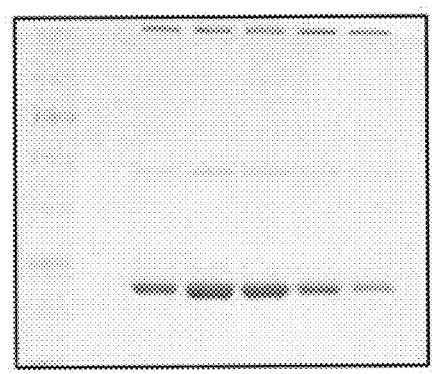
FIG. 2D is an image of electrophoresis results of an AP1 peptide-inserted fusion protein after purification where a ferritin having AP1L is inserted in GP cassette.
Figure 3:
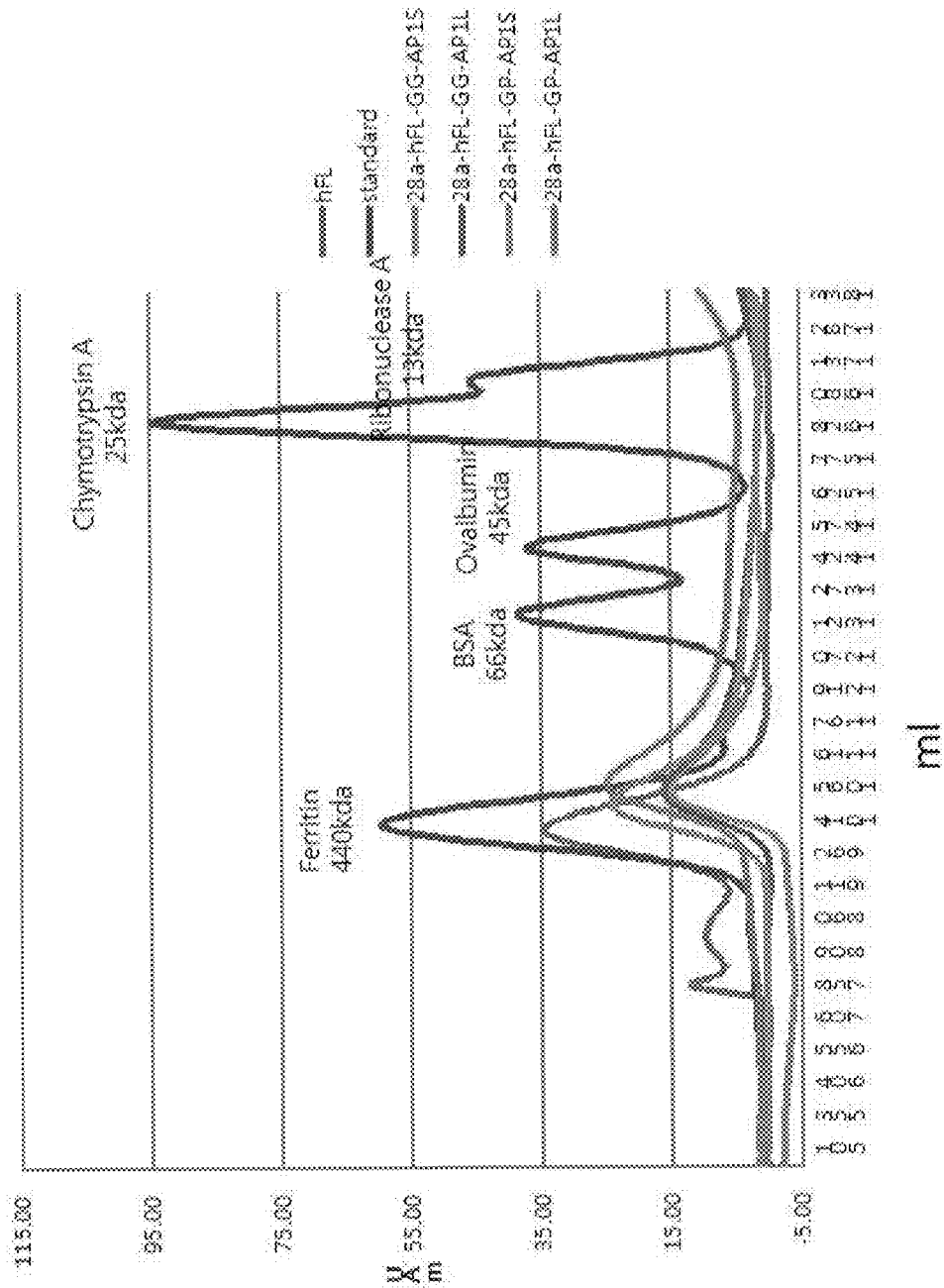
FIG. 3 is a graph showing a fast protein liquid chromatography (FPLC) result of expressed fusion proteins (FTL: human ferritin light chain, FTL-GG-AP1S: ferritin having AP1S inserted in GG cassette, FTL-GG-AP1L: ferritin having AP1L inserted in GG cassette, FTL-GP-AP1S: ferritin having AP1S inserted in GP cassette, FTL-GP-AP1L: ferritin having AP inserted in GP cassette).
Figure 4A:
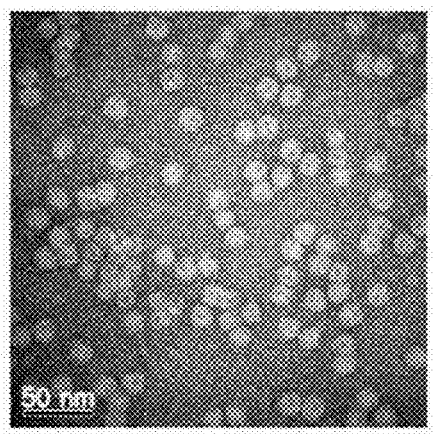
FIG. 4A is an electron microscope image showing protein cages formed of produced fusion proteins by wild type ferritins without AP1 insertion.
Figure 4B:
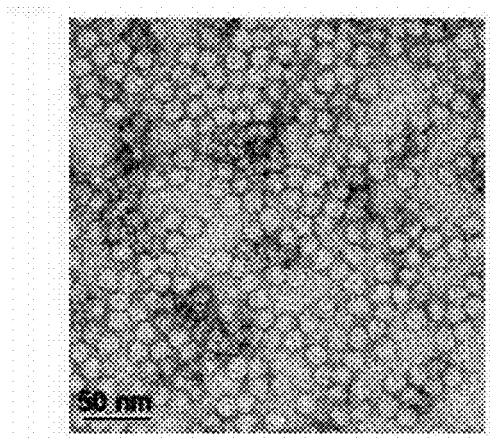
FIG. 4B is an electron microscope image showing protein cages formed of produced fusion proteins by ferritins having AP1S inserted in a GG cassette.
Figure 4C:
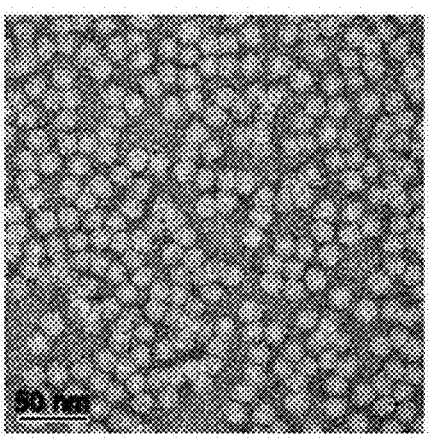
FIG. 4C is an electron microscope image showing protein cages formed of produced fusion proteins by ferritins having AP inserted in a GG cassette.
Figure 4D:
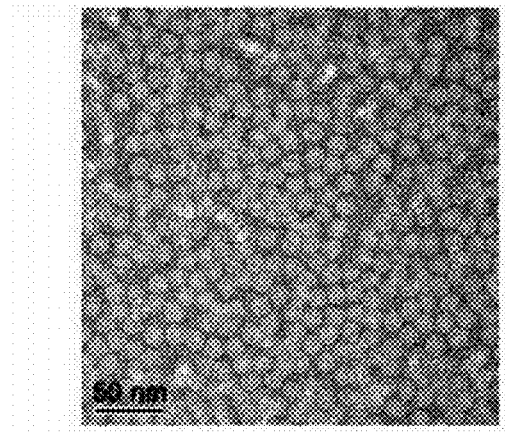
FIG. 4D is an electron microscope image showing protein cages formed of produced fusion proteins by ferritins having AP1S inserted in a GP cassette.
Figure 4E:
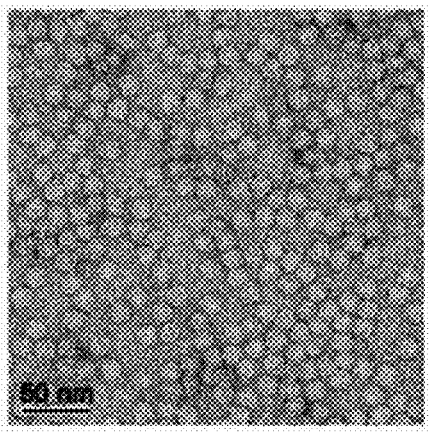
FIG. 4E is an electron microscope image showing protein cages formed of produced fusion proteins by ferritins having AP1L inserted in a GP cassette.
Figure 5A:
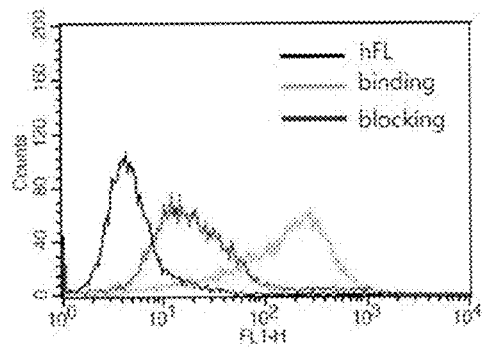
FIG. 5A is a graph showing FACS measurement results for investigating whether AP1 peptide-inserted ferritins bind to IL-4 receptor for ferritins having AP1S inserted in a GG cassette (FTL: wild type human-derived ferritin, binding: AP1-bound human-derived ferritin, blocking: test results after IL-4 receptor was blocked with IL-4 receptor antibody, FL1-H: the fluorescence intensity per cell, count: cell count).
Figure 5B:
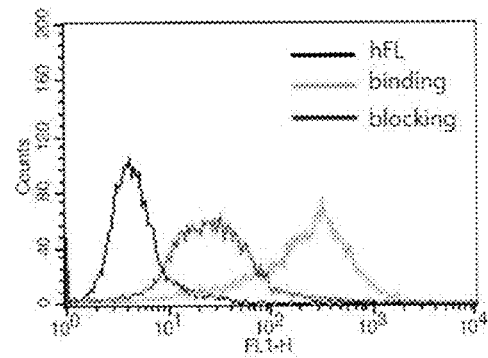
FIG. 5B is a graph showing FACS measurement results for investigating whether AP1 peptide-inserted ferritins bind to IL-4 receptor for ferritins having AP1L inserted in a GG cassette (FTL: wild type human-derived ferritin, binding: AP1-bound human-derived ferritin, blocking: test results after IL-4 receptor was blocked with IL-4 receptor antibody, FL1-H: the fluorescence intensity per cell, count: cell count).
Figure 5C:
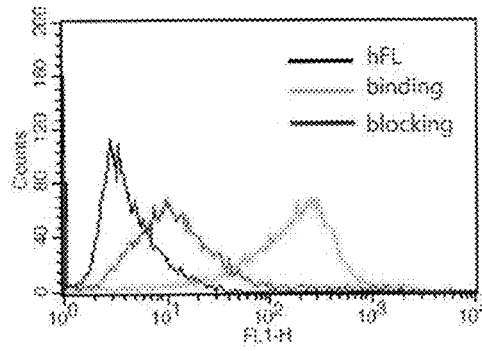
FIG. 5C is a graph showing FACS measurement results for investigating whether AP1 peptide-inserted ferritins bind to IL-4 receptor for ferritins having AP1S inserted in a GP cassette (FTL: wild type human-derived ferritin, binding: AP1-bound human-derived ferritin, blocking: test results after IL-4 receptor was blocked with IL-4 receptor antibody, FL1-H: the fluorescence intensity per cell, count: cell count).
Figure 5D:
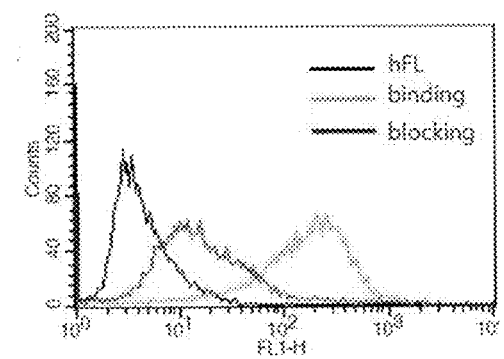
FIG. 5D is a graph showing FACS measurement results for investigating whether AP1 peptide-inserted ferritins bind to IL-4 receptor for ferritin having AP1L inserted in a GP cassette (FTL: wild type human-derived ferritin, binding: AP1-bound human-derived ferritin, blocking: test results after IL-4 receptor was blocked with IL-4 receptor antibody, FL1-H: the fluorescence intensity per cell, count: cell count).
Figure 6A:
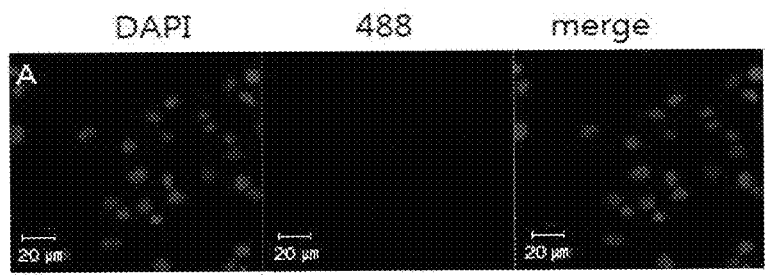
FIG. 6A is a confocal microscope observation image investigating whether AP1 peptide-inserted ferritins bind to IL-4 receptor for wild type ferritins without AP1 insertion (DAPI: images of cells stained with 4',6-diamidino-2-phenylindole, 488: images for Alexa Fluor 488 donkey anti-goat IgG-specific imaging, merge: composite of DAPI and 488 images.
Figure 6B:
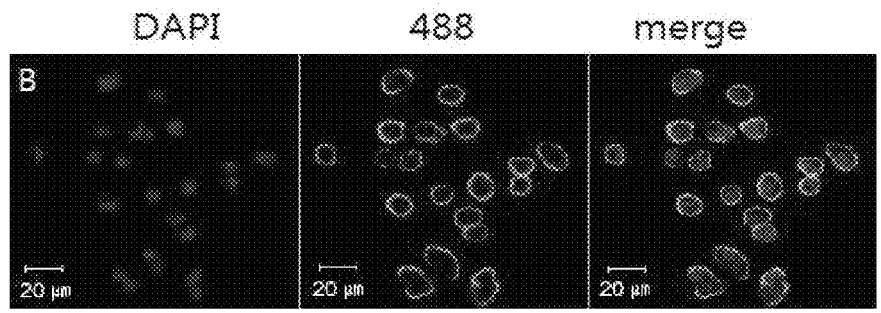
FIG. 6B is a confocal microscope observation image investigating whether AP1 peptide-inserted ferritins bind to IL-4 receptor for ferritins having AP1S inserted in a GG cassette (DAPI: images of cells stained with 4',6-diamidino-2-phenylindole, 488: images for Alexa Fluor 488 donkey anti-goat IgG-specific imaging, merge: composite of DAPI and 488 images.
Figure 6C:
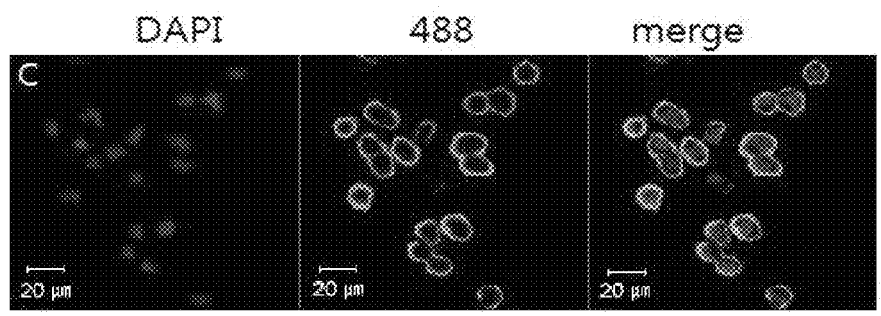
FIG. 6C is a confocal microscope observation image investigating whether AP1 peptide-inserted ferritins bind to IL-4 receptor for ferritins having AP1L inserted in a GG cassette.
Figure 6D:
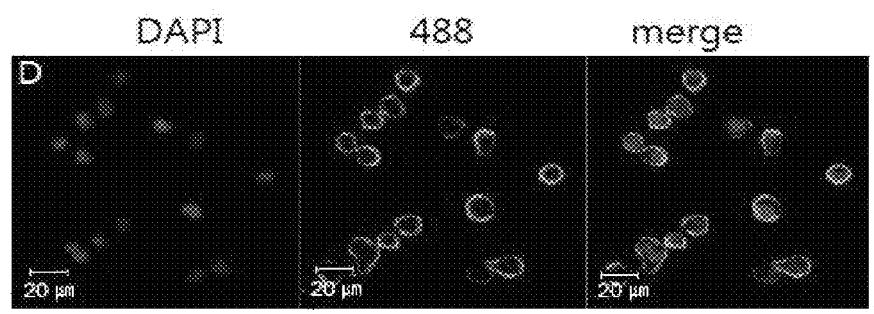
FIG. 6D is a confocal microscope observation image investigating whether AP1 peptide-inserted ferritins bind to IL-4 receptor for ferritins having AP1S inserted in a GP cassette (DAPI: images of cells stained with 4',6-diamidino-2-phenylindole, 488: images for Alexa Fluor 488 donkey anti-goat IgG-specific imaging, merge: composite of DAPI and 488 images.
Figure 6E:
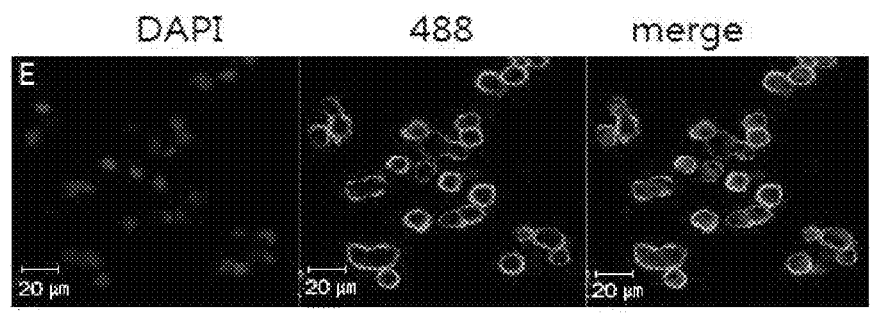
FIG. 6E is a confocal microscope observation image investigating whether AP1 peptide-inserted ferritins bind to IL-4 receptor for ferritins having AP1L inserted in GP cassette, (DAPI: images of cells stained with 4',6-diamidino-2-phenylindole, 488: images for Alexa Fluor 488 donkey anti-goat IgG-specific imaging, merge: composite of DAPI and 488 images).
Figure 7A:
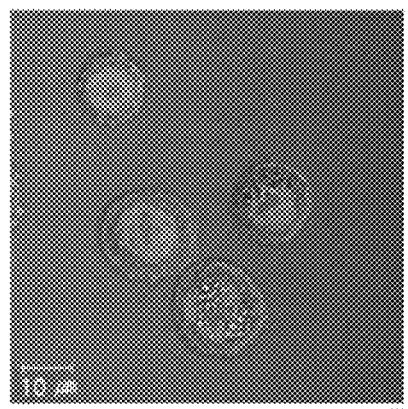
FIG. 7A is a microscope observation image investigating the uptake of AP1 peptide-inserted ferritins into cells by binding to IL-4 receptor for wild type ferritins without AP1 insertion.
Figure 7B:
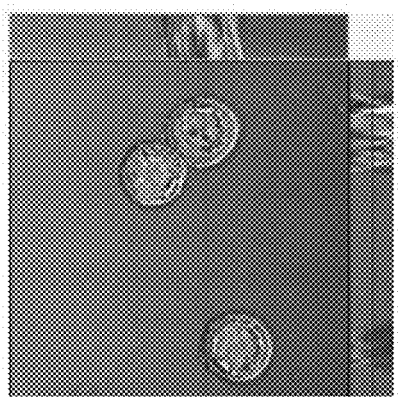
FIG. 7B is a microscope observation image investigating the uptake of AP1 peptide-inserted ferritins into cells by binding to IL-4 receptor for ferritins having AP1S inserted in a GG cassette.
Figure 7C:
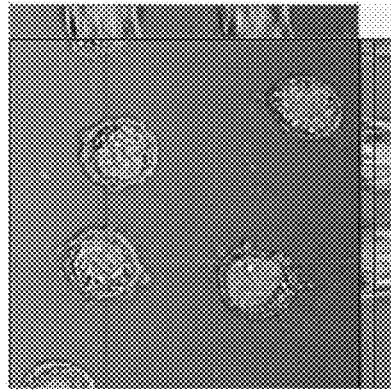
FIG. 7C is a microscope observation image investigating the uptake of AP1 peptide-inserted ferritins into cells by binding to IL-4 receptor for ferritins having AP1L inserted in a GG cassette.
Figure 7D:
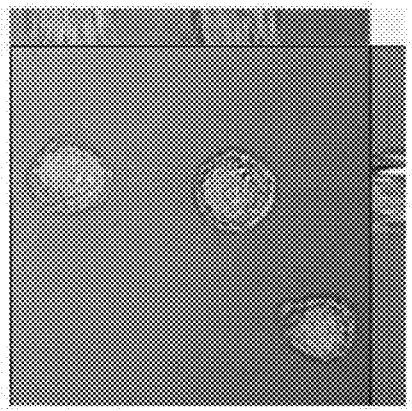
FIG. 7D is a microscope observation image investigating the uptake of AP1 peptide-inserted ferritins into cells by binding to IL-4 receptor for ferritins having AP1 S inserted in a GP cassette.
Figure 7E:
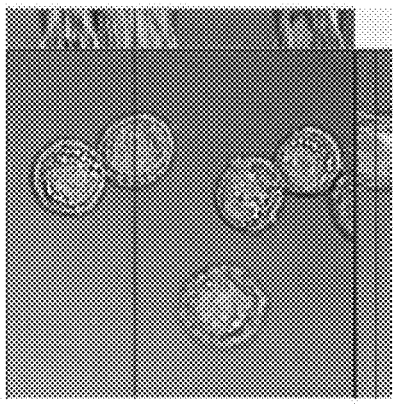
FIG. 7E is a microscope observation image investigating the uptake of AP1 peptide-inserted ferritins into cells by binding to IL-4 receptor for ferritin having AP1L inserted in GP cassette.

The present invention provides a fusion polypeptide in which a first polypeptide fragment composed of 5 to 30 amino acids is fused between the first and the fifth amino acids of the fourth loop of a human-derived ferritin monomer.

Ferritin is a kind of intracellular protein, and functions to store and release iron. Ferritin is generally in the form of a hollow spherical cage in vivo. The cage is composed of 24 ferritin monomers, and the ferritin monomers are divided into heavy chain monomers and light chain monomers depending on the structure thereof.

As for the ferritin monomer of the present invention, all forms of ferritin monomers may be used regardless of the structure of the ferritin monomer. The ferritin monomer may be, preferably, a ferritin light chain, and more preferably a polypeptide that may include an amino acid sequence represented by SEQ ID NO: 1. The amino acid sequence represented by SEQ ID NO: 1 is a light chain of a human-derived ferritin protein.

The structure of the ferritin monomer has a form in which five alpha helix structures are sequentially connected, while amorphous polypeptide moieties that connect respective alpha helix structured polypeptides are called loops.

The fourth loop of the present invention refers to a loop located between the fourth and the fifth alpha-helix structured polypeptides of the human-derived ferritin monomer.

The fusion polypeptide of the present invention is characterized in that a first polypeptide fragment including 5 to 30 amino acids is fused between the first and the fifth amino acids of the fourth loop of the human-derived ferritin monomer.

As for the fusion polypeptide of the present invention, the first polypeptide fragment may be fused to anywhere between the first and the fifth amino acids of the fourth loop of the human-derived ferritin monomer. For example, the first polypeptide fragment may be fused between the first and the second amino acids, between the second and the third amino acids, between the third and the fourth amino acids, or between the fourth and the fifth amino acids.

Between the first and the fifth amino acids of the fourth loop of the human-derived monomer in the fusion polypeptide of the present invention may be between the 154$^{th}$ and the 158$^{th}$ amino acids of the amino acid sequence represented by SEQ ID NO: 1, for example, between the 154$^{th}$ and the 155$^{th}$ amino acids, between the 155$^{th}$ and the 156$^{th}$ amino acids, between the 156$^{th}$ and the 157$^{th}$ amino acids, or between the 157$^{th}$ and the 158$^{th}$ amino acids, of the amino acid sequence represented by SEQ ID NO: 1.

In addition, in the fusion polypeptide of the present invention, the first polypeptide fragment is fused, while some of the first to the fifth amino acids of the fourth loop may be deleted. Alternatively, the first polypeptide fragment may be substituted with some of the first to the fifth amino acids of the fourth loop. Since such a deletion or substitution induces no great change in the structure of the fusion polypeptide, the binding between the fusion polypeptides or between the fusion polypeptide and the human-derived ferritin monomer favorably occurs, and the improvement in the binding specificity of the fused first polypeptide fragment is also maintained.

As for the deletion, one of the first to the fifth amino acids of the fourth loop may be deleted, or multiple amino acids thereof may be deleted. As for the substitution, one of the first to the fifth amino acids of the fourth loop may be substituted with the first polypeptide fragment of the present invention, and multiple amino acids thereof may be substituted with the first polypeptide fragment of the present invention. In an example of the present invention, as for a fusion polypeptide which includes amino acids represented by SEQ ID NO: 2 or 3, the first polypeptide fragment was fused between the 154$^{th}$ and the 155$^{th}$ amino acids, and the 155$^{th}$ amino acid was deleted.

In addition, the fusion polypeptide of the present invention is characterized by specifically binding to a target material. The target material refers to a material exhibiting binding affinity to the first or second polypeptide fragment fused in the fusion polypeptide of the present invention.

As for the target material, any kind of material may be used including in vivo materials and ex vivo materials. The in vivo materials include in vivo organs, tissues, cells, receptors on cell surfaces, intracellular proteins containing enzymes, intercellular materials, nucleic acids, toxic materials entering from the outside, therapeutic materials, and inspection materials.

The ex vivo materials include supports for fixating materials for various tests (various kinds of resins, slide glasses, plates, and films) or organic and inorganic compounds as targets for various kinds of tests.

The research staffs of the present invention verified that, with respect to the fusion polypeptide, in which the polypeptide fragment is fused between the first and the fifth amino acids of the fourth loop of the human-derived ferritin monomer represented by SEQ ID NO: 1, a spherical cage is formed by binding between the fusion polypeptides or between the fusion polypeptide and another ferritin monomer, and here, the polypeptide fragment included in the fusion polypeptide of the present invention protrudes outwardly from the spherical cage, and thus can specifically bind to a target material. Particularly, in cases where, like the fusion polypeptide of the present invention, the polypeptide fragment is fused between the first and the fifth amino acids of the fourth loop of the ferritin monomer, the target-specific binding affinity of the fused polypeptide fragment is significantly enhanced, and thus can bind to even a material at its significantly low concentration. This subject matter is first disclosed in the present invention.

The first polypeptide fragment of the present invention is a polypeptide which is fused between the first and the fifth amino acids of the fourth loop of the human-derived ferritin monomer, while its length thereof or the arrangement of its constituent amino acids is not limited, but, preferably, the first polypeptide fragment may include 5 to 30 amino acids.

Meanwhile, the first polypeptide fragment of the present invention may be represented by sequence general formula (I) below:

[N terminal-X1-X2-X3-C terminal]  General formula (I)

wherein X1 and X3 each are a linker that includes 1 to 3 amino acids; and X2 is an active polypeptide that includes 1 to 28 amino acids.

The first polypeptide fragment may be a polypeptide fragment having any amino acid sequence, and preferably may include an active polypeptide.

The active polypeptide is a peptide exhibiting intended activity, and may be, for example, a peptide exhibiting a binding activity to particular molecules, cells, or tissues.

In addition, the first polypeptide fragment may include a linker. The linker is for attaching the active polypeptide to a particular site of the light chain of the human-derived ferritin protein represented by SEQ ID NO: 1. The linker includes one to several amino acids, and preferably, 1 to 3 amino acids, while, more preferably, the linker may be a cleavage site of a particular protein restriction enzyme.

Preferably, linker X1 may be glycine-serine, and linker X3 may be glycine-proline or glycine-glycine-proline.

The length of the active polypeptide is not limited as long as the frame structure of the fusion polypeptide is maintained, and thus the active polypeptide may includes, for example, 5 to 28 amino acids, and preferably, 7 to 9 amino acids.

Most preferably, the active polypeptide may be an active polypeptide represented by a sequence selected from the group consisting of SEQ ID NO: 6 (AP1S), SEQ ID NO: 7 (AP1L), SEQ ID NO: 33 (RGD), and SEQ ID NO: 34 (GRGDSP).

Meanwhile, in the fusion polypeptide of the present invention, the first polypeptide fragment may include 5 to 30 amino acids that are fused between the first and the fifth amino acids of the fourth loop of the human-derived ferritin monomer, while a second polypeptide fragment may includes 5 to 30 amino acids that may be additionally fused to N-terminal of the fusion polypeptide.

The second polypeptide fragment is a polypeptide fused to N-terminal of the human-derived ferritin monomer of the present invention, and the length thereof or the arrangement of constituent amino acids thereof is not limited, but, preferably, the second polypeptide fragment may include 5 to 30 amino acids. In addition, it is preferable not to interrupt the binding between the fusion polypeptides or between the fusion polypeptide and a human-derived ferritin monomer.

The second polypeptide fragment may include the same active polypeptide as the first polypeptide, or may include a different active polypeptide from the first polypeptide.

The fusion polypeptide, in which the first polypeptide fragment and the second polypeptide fragment are, respectively, fused between the first and the fifth amino acids of the fourth loop and to the N-terminal of the human-derived ferritin monomer, binds to target molecules, cells, or tissues more effectively than the fusion polypeptide in which only the first polypeptide fragment is fused.

The fusion polypeptide of the present invention may be, preferably, a fusion polypeptide includes an amino acid sequence selected from the group consisting of SEQ ID NOs: 2 to 5, or an amino acid sequence selected from the group consisting of SEQ ID NOs: 23, 25, 27, 29, and 31.

Meanwhile, the polypeptide fragment of the present invention may be characterized by not interrupting the binding between the fusion polypeptides or between the fusion polypeptide and the human-derived ferritin monomer.

The fusion polypeptide of the present invention can be used alone, without the binding between the fusion polypeptides or between the fusion polypeptide and another ferritin monomer. However, like ferritin, dimers or trimers may be formed through the binding between the fusion polypeptides or between the fusion polypeptide and another ferritin monomer, or several monomers form a cage protein to exhibit new functions or further enhance the binding specificity to the other materials. Therefore, preferably, the polypeptide fragment of the present invention does not interrupt the binding between the fusion polypeptides or between the fusion polypeptide and the human-derived ferritin monomer.

The fusion polypeptide of the present invention is, but not limited to, preferably, inserted into a normal vector, which is constructed so as to express a foreign gene, to be able to be expressed, and thus can be mass-produced in a genetic engineering manner. The vector may be appropriately selected or newly constructed depending on the kind and characteristics of host cells for producing proteins. The method for transforming host cells with the vector and the method for producing a recombinant protein from a transformant may be easily carried out by conventional methods.

The methods for selection and construction of the vector, transformation, expression of the recombinant protein, and the like, may be easily carried out by a person skilled in the art to which the present invention pertains, and some modifications in conventional methods may be also included in the present invention.

Meanwhile, the present invention provides a polynucleotide encoding the fusion polypeptide of the present invention.

As for the polynucleotide of the present invention, any nucleotide sequence that can encode the fusion polypeptide of the present invention may be used. Preferably, the polynucleotide of the present invention may be represented by any nucleotide sequence selected from the group consisting of SEQ ID NOs: 9 to 12. In addition, the fusion polypeptide may be represented by a nucleotide sequence selected from the group consisting of SEQ ID NOs: 24, 26, 28, 30, and 32.

Meanwhile, the present invention provides an expression vector including the polynucleotide of the present invention.

The expression vector of the present invention is characterized by including the polynucleotide of the present invention, and the kind thereof includes a plasmid vector, a cosmid vector a bacteriophage vector, and a viral vector, but is not limited thereto. The expression vector of the present invention may be a normal expression vector, and the expression vector includes signal sequences for membrane targeting or secretion, or reader sequences, as well as expression regulatory sequences, such as a promoter, an operator, an initiation codon, a termination codon, a polyadenylation signal, and an enhancer (promoter gene), and may be variously prepared depending on the purpose thereof. The promoter of the expression vector may be constitutive or inducible. In addition, the vector includes a selective marker for selecting a host cell containing the vector, and includes a replication origin in the case of a replicable vector.

Meanwhile, the present invention provides a transformant transformed with the expression vector of the present invention.

The transformant of the present invention is characterized by being transformed with the expression vector of the present invention. The transformation with the expression vector may be carried out by the transformation technique known to a person skilled in the art. Preferably, examples of the transformation technique may include microprojectile bombardment, electroporation, Calcium phosphate ($CaPO_4$) precipitation, calcium chloride ($CaCl_2$) precipitation, PEG-mediated fusion, microinjection, and liposome-mediated method. Examples of the transformant may include *Escherichia coli, Bacillus subtilis, Streptomyces, Pseudomonas, Proteus mirabilis, Staphylococcus, Agrobacterium tumefaciens*, but are not limited thereto.

Meanwhile, the present invention provides a protein cage including the fusion polypeptide of the present invention. Furthermore, the present invention provides a ferritin protein including the fusion polypeptide of the present invention.

The protein cage is formed by a precise self-assembling property of low-molecular weight monomers, and has a space therein. Viral capsid proteins, ferritins, heat shock proteins, and Dps proteins belong to the protein cage. The protein cage of the present invention is characterized by including the fusion polypeptide of the present invention as a monomer constituting the protein cage. The protein cage of the present invention may include only the fusion polypeptide of the present invention, or a combination of the fusion polypeptide of the present invention and another ferritin protein monomer.

The ferritin protein of the present invention is made by the binding of ferritin protein monomers, and is generally in the form of a spherical cage in vivo.

The ferritin protein of the present invention may be a complex protein in which the fusion polypeptides of the present invention are regularly arranged as monomers, and may be formed through a three-dimensional regular arrangement of 24 fusion polypeptides of the present invention.

In an example of the present invention, BamH1 and Apa1 restriction enzyme sites were introduced into the human ferritin light chain to prepare cassettes, and two kinds of AP1 peptides were inserted in the cassettes. This was put into *E. coli* expression vector pET28a to construct an expression vector, and *E. coli* was transformed with the expression vector to mass-produce the fusion polypeptide. The prepared protein was separated and purified using affinity column. The SDS-PAGE analysis results of the purified protein verified that the fusion polypeptide of the present invention was prepared.

In another example of the present invention, it was investigated through FPLC and electron microscopy imaging whether the prepared fusion polypeptide forms a cage like its wild type. The results verified that the fusion polypeptide of the present invention favorably formed a cage.

In another example of the present invention, in order to find out whether the active polypeptide included in the prepared fusion polypeptide exhibits an intended activity, it was investigated whether the fusion polypeptide binds to the IL-4 receptor. In the example, AP1 peptide used as an active polypeptide has characteristics of binding to the IL-4 receptor. As a result of allowing the fusion polypeptide of the present invention, which is the AP1 peptide-bound ferritin, and the wild type ferritin, which is the AP1 peptide-not-bound ferritin, to bind to A549 cells expressing IL-4 at a high level, it was verified that the AP1-bound fusion polypeptide of the present invention favorably bound to A549 cells, whereas the AP1-not-bound wild type ferritin did not bind to A549 cells.

In another example of the present invention, it was investigated through confocal microscope observation whether the AP1-bound fusion polypeptide of the present invention invades into A549 cells. As a result, it was verified that the fusion polypeptide of the present invention showed a favorable uptake into A549 cells after binding to the target cells.

In another example of the present invention, it was investigated through surface plasmon resonance analysis whether the binding affinity of the active polypeptide increases by the fusion polypeptide of the present invention. The test results verified that, the fusion polypeptide of the present invention including AP1 was $10^5$-$10^6$ times higher than AP1 peptide alone in view of binding affinity to IL-4 receptor.

Meanwhile, in another example of the present invention, a fusion polypeptide, in which the first and the second polypeptide fragments, which contain AP1 peptides as active polypeptides, respectively, were fused between the first and the fifth amino acids of the fourth loop and to N-terminal of the human-derived ferritin monomer, was prepared.

In another example of the present invention, the binding affinity of the fusion polypeptide in which the first and the second polypeptide fragments were fused was compared with that of the fusion polypeptide in which only the first polypeptide fragment was fused. The results verified that the binding affinity of the fusion polypeptide in which the first and the second polypeptide fragments were fused was 10 times higher than that of the fusion polypeptide in which only the first polypeptide fragment was fused.

In another example of the present invention, it was investigated through electron microscope observation whether the fusion polypeptide in which the first and second polypeptide fragments are fused favorably forms a protein cage. The results verified that the fusion polypeptide of the present invention in which the first and second polypeptide fragments were fused favorably formed a protein cage like the human-derived ferritin monomer or the fusion polypeptide of the present invention in which only the first polypeptide fragment was fused.

Thus, it was verified that the fusion polypeptide of the present invention favorably forms a cage and enhances the binding affinity of the active polypeptide included therein.

In another example of the present invention, a fusion polypeptide in which the first polypeptide is different from the second polypeptide was prepared, and then the cage formation and the target binding affinity thereof were measured. Besides AP1, RGD peptide, which binds to integrin alphavbeta3 protein, was fused in the fusion polypeptide, and then the binding affinity thereof to integrin alphavbeta3 protein was analyzed through SPR. The results verified that the fusion polypeptide bound to integrin alphavbeta3 protein in a concentration-dependent manner. In addition, the cage formation was verified through FPLC analysis and electron microscope observation.

Therefore, the present invention provides a drug delivery system containing the fusion polypeptide of the present invention as an active ingredient.

The drug delivery system of the present invention is characterized by containing the fusion polypeptide of the present invention as an active ingredient.

The drug may be, for example, a drug having activity to treat or prevent a particular disease or a drug for diagnosis. The particular disease may be any disease that can be treated or prevented by the drug. Preferably, the particular disease may be cancer, allergy, arteriosclerosis, or asthma. The drug may be any kind of known material, such as a chemically synthesized compound, a protein therapeutic agent, and a nucleic acid, and may be, preferably, a chemically synthesized compound, a protein therapeutic agent, and a nucleic acid such as siRNA, for treating cancer, allergy, arteriosclerosis, or asthma.

The fusion polypeptide of the present invention may form a protein cage, and the drug may be contained inside the formed protein cage. In addition, the fusion polypeptide of the present invention can specifically bind to molecules, cells, or tissues by exposing an active polypeptide thereof outwardly from the protein cage when the protein cage is formed, and thus the fusion polypeptide of the present invention can be used as a drug delivery system that selectively delivers the drug to target molecules, cells, or tissues.

In addition, the first or the second polypeptide fragment fused in the fusion polypeptide of the present invention may be composed of a drug-bindable polypeptide. In this case, the fusion polypeptide of the present invention may be used as a drug delivery system in which the drug is delivered by binding to the first or second polypeptide fragment.

In addition, the fusion polypeptide of the present invention may be prepared by including a polypeptide, which has effects of treating, diagnosing, and preventing a particular disease, of the first or the second polypeptide fragment of the present invention. In this case, the fusion polypeptide of the present invention may be used a drug delivery system which delivers the first or the second polypeptide fragment, which is the drug.

The drug delivery system of the present invention may target various cells, tissues, and diseases depending on the kind of polypeptide fragment fused in the fusion polypeptide of the present invention.

In one example of the present invention, a fusion polypeptide, which is a part of the first or the second polypeptide fragment fused in the fusion polypeptide of the present invention, specifically binds to the interleukin-4 receptor, and is represented by SEQ ID NO: 6 or 7, was prepared, and the specific binding thereof to interleukin-4 receptor was verified.

Therefore, the drug delivery system of the present invention may be, preferably, a drug delivery system that specifically targets the interleukin-4 receptor, and more preferably, the drug delivery system of the present invention may be a drug delivery system that contains, as an active ingredient, a fusion polypeptide including an amino acid sequence selected from the group consisting of SEQ ID NOs: 2-5, 23, 25, 27, 29, and 31.

In another example of the present invention in which asthma animal models were prepared, its inhibition to asthma was verified by administering an AP-1-containing ferritin cage and a control (ferritin cage not containing AP-1) to the asthma animal models.

The results confirmed that asthma symptoms, such as airway hyper-responsiveness (AHR), the inflammatory cell count or eosinophil count in bronchial alveolar lavage (BAL) fluid, and the level of secreted glycoprotein, were mitigated in the group administered with AP-1-containing ferritin cage rather than in the control.

Therefore, the present invention provides an agent for treating asthma including, as an active ingredient, a fusion polypeptide including an amino acid sequence selected from the group consisting of SEQ ID NOs: 2-5, 23, 25, 27, 29, and 31.

AP-1 is a peptide that specifically binds to the interleukin-4 receptor. In another example of the present invention, it was verified that the AP-1-containing fusion polypeptide of the present invention specifically binds to the interleukin-4 receptor. Therefore, the fusion polypeptide of the present invention binds to the interleukin-4 receptor competitively with interleukin-4, and thus can be used for treating interleukin-4-mediated disease.

Therefore, the present invention provides a pharmaceutical composition for preventing or treating interleukin-4 mediated disease, the composition including the fusion polypeptide as an active ingredient.

Furthermore, the present invention provides a method for preventing or treating interleukin-4 mediated disease, the method including administering an effective amount of the fusion polypeptide to a subject in need thereof.

Still furthermore, the present invention provides a use of the fusion polypeptide for preparing an agent for preventing or treating interleukin-4 mediated disease.

The pharmaceutical composition according to the present invention may contain the fusion polypeptide of the present invention alone or may further contain at least one pharmaceutically acceptable carrier. As used herein, the "effective amount" refers to an amount required to exhibit a higher effect as compared with a negative control, and, preferably, an amount sufficient to treat interleukin-4 mediated disease.

The term "subject" refers to an animal, preferably a mammal, and especially, an animal including a human being, and may be cells, tissues, organs, or the like, derived from the animal. The subject may be a patient in need of treatment.

As used herein, the term "pharmaceutically acceptable" refers to a non-toxic composition that is physiologically acceptable, does not inhibit the action of an active ingredient when administered to humans, and does not normally cause an allergic reaction or similar reactions, such as gastroenteric troubles and dizziness.

The composition of the present invention is characterized by containing the fusion polypeptide of the present invention as an active ingredient. Preferably, the composition of the present invention may be a composition containing, as an active ingredient, a fusion polypeptide including an amino acid sequence selected from the group consisting of SEQ ID NOs: 2-5, 23, 25, 27, 29, and 31.

Interleukin-4 (IL-4) is a cytokine with various immunoregulatory functions, which is secreted from T-helper 2 (Th2) lymphocytes, eosinophils, mast cells, and the like. IL-4 receptors are found on cellular surfaces of normal T lymphocytes, B lymphocytes, and CD34 myelocytes (Nelms, Annu Rev Immunol, 1999; 17:701-738). There are two types in IL-4 receptors, type 1 receptors in which IL-4 receptor α chain and IL-2 receptor γc chain constitute complexes, and type 2 receptors in which IL-4 receptor α chain and IL-13 receptor α1 chain constitute complexes. The binding between IL-4 and its receptor leads to phosphorylation and activation of STAT6 signal protein through Janus kinase in cells, and the activated STAT6 protein migrates into the nucleus in a dimer form and regulates the expression of several genes associated with IL-4, thereby increasing inflammation. In addition, AKT/PKB is activated through Janus kinase, thereby increasing cell survival (Nelms et al., Annu Rev Immunol, 1999; 17:701-738). IL-4 induces the differentiation of naive T-helper (Th) into Th2 lymphocytes and the production of cytokines, such as IL-4, IL-5, IL-9, and IL-13. Also, IL-4 induces the secretion of immunoglobulin E (IgE) by B lymphocytes. It has been known that, particularly in asthma, IL-4 plays an important role in airway obstruction and inflammation by inducing the expression of the gene of mucin, which is the pituitary protein, and promoting mucous secretion (Paul, Blood, 1991; 77:1859-1870). As such, IL-4 is a key material in the allergic inflammatory response. Therefore, it is thought that the proper inhibition of IL-4-mediated effects may be favorably applied to the treatment of allergic diseases.

Meanwhile, IL-4 is found at a higher concentration in arteriosclerotic tissues rather than in normal tissues, and induces the expression of VCAM-1 and MCP-1 in vascular endothelial cells to promote the migration of monocytes, T lymphocytes, basophils, and eosinophils into inflammatory sites (Sasaguri et al., Atherosclerosis, 1998; 138:247-253; Lee et al., J Mol Cell Cardiol, 2001; 33:83-94). More importantly, it was reported that, when genetic deficiency of IL-4 is introduced into an LDL receptor- or ApoE-deficient atherosclerosis mouse model, the size of the aortic atherosclerotic lesion decreases (Davenport et al., Am J Pathol, 2003; 163:1117-1125; King et al., Arterioscler Thromb Vasc Biol, 2002; 22:456-461). As such, IL-4 is implicated in the atherosclerotic development, and the antagonizing IL-4 activity will produce effects of treating or preventing atherosclerosis.

In addition, it was reported that IL-4 is found at a higher concentration in several cancer tissues rather than in normal tissues, and a large amount of IL-4 is produced in tumor-infiltrating lymphocytes (TILS) (Shurin, Springer Semin Immunopathol, 1999; 21:339). IL-4 acts on chronic lymphocytic leukemia B cells to induce a resistance to apoptotic cell death (Dancescu, J Exp Med, 1992; 176:1319). In addition, it was recently reported that, IL-4 is synthesized in tumor cells and cancer stem cells, and gives a resistance of cancer cells to apoptosis through the IL-4 receptor on the cancer cell surfaces (Todaro, Cell Death Differ, 2008; 15:762-772; Todaro, Cell Stem Cell, 2007, 1:389-402). The expression level of IL-4 receptor is higher in various cancer cells including non-small cell lung cancer, brain tumor, breast cancer, bladder cancer, pancreatic cancer, prostate cancer, kidney cancer, and Kaposi's sarcoma, rather than in normal cells. In consideration of the acquisition of anticancer agent resistance by cancer cells through the IL-4 receptor and the high expression level of the IL-4 receptor in cancer cells, the IL-4 receptor may be a promising target for cancer therapy. Researches about cancer cell death through the introduction of toxin into cells while targeting cancer cells using a fusion protein obtained by combining partially modified IL-4 with pseudomonas toxin have been reported (Joshi, Cancer Res, 2001; 61:8058-8061; Garland, J Immunother, 2005; 28:376-381; Kioi, Cancer Res, 2005; 65:8388-8396; Kawakami, Clin Cancer Res, 2002; 8:3503-3511).

Meanwhile, a variety of antagonists for IL-4 itself have been developed as therapeutic agents for asthma or the like. For example, Immunex Company developed Nuvance, which is a soluble form of IL-4 receptor, and tested it in clinical trials as an asthma therapeutic agent, but its development was discontinued due to its insufficient therapeutic effects. In addition, Glaxosmithkline Company developed Pascolizumab, which is a monoclonal antibody to IL-4, and tested it in clinical trials, but its development was stopped. Bayer Company developed Pitrakinra, which is a modified IL-4 protein having two mutants, and is being tested in clinical trials. Sunesis Pharm. Inc developed triphenyl compounds as IL-4 antagonists, and is being tested in clinical trials (WO 2001/098245).

Therefore, the interleukin-4-mediated disease of the present invention may be, preferably, selected from the group consisting of cancer, allergy, arteriosclerosis, and asthma.

Preferable examples of the cancer include epithelial squamous cell cancer, uterine cancer, cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, kidney cancer, bladder cancer, ovarian cancer, cholangiocarcinoma, gallbladder carcinoma, and the like, but are not limited thereto.

In the pharmaceutical composition according to the present invention, the fusion polypeptide may be administered in several oral or parental dosage forms at the time of clinical administration, and may be formulated by using a diluent or a vehicle, such as a filler, an extender, a binder, a wetting agent, a disintegrant, or a surfactant, which are normally used.

Solid preparations for oral administration include a tablet, a pill, a powder, granules, a capsule, a troche, and the like. These solid preparations may be prepared by mixing a least one fusion polypeptide of the present invention with at least one vehicle, for example, starch, calcium carbonate, sucrose or lactose, gelatin, or the like. In addition to simple vehicles, lubricants, such as magnesium stearate and talc, may be used. Liquid preparations for oral administration include a suspension, an oral solution, an emulsion, a syrup, and the like. Besides simple diluents that are frequently used, such as water and liquid paraffin, several vehicles, for example, a wetting agent, a sweetener, an aroma, and a preservative may be included in the liquid preparations.

Preparations for parenteral administration include a sterilized aqueous solution, a non-aqueous solvent, a suspension solvent, an emulsion, a freeze-drying agent, and a suppository.

The composition for treatment of the present invention may be prepared in the form of a freeze-dried cake or an aqueous solution in order to mix any physiologically acceptable carrier, vehicle, or stabilizer (Remington: The Science and Practice of Pharmacy, 19th Edition, Alfonso, R., ed, Mack Publishing Co. (Easton, Pa.: 1995)) with an antibody having preferable purity and store the mixture. The acceptable carrier, vehicle, or stabilizer is non-toxic to a user at used dose and concentration, and includes: buffers, for example, phosphoric acid, citric acid, and other organic acids; antioxidants including ascorbic acids; low-molecular weight (less than about 10 residues) polypeptides; proteins, for example, serum albumin, gelatin, or immunoglobulin; hydrophilic polymers, for example, polyvinyl pyrrolidone; amino acids, for example, glycine, glutamine, asparagine, arginine, or lysine; monosaccharides, disaccharides, and other carbohydrates including glucose, mannose, or dextrin; chelating agents, for example, EDT; sugar alcohols, for example, mannitol or sorbitol; salt-forming counter ions, for example, sodium; and/or non-ionic surfactants, for example, Tween, pluronics, or polyethylene glycol (PEG).

In addition, the administration of the fusion polypeptide of the present invention to the human body may be performed on a patient in a single dose, and may be performed in a multiple dose by fractionated treatment protocol for a long period of time. In the pharmaceutical composition of the present invention, the content of the active ingredient may vary depending on the severity of disease. A preferable daily dose of the fusion polypeptide of the present invention may be about 0.0001 mg to 100 mg, and most preferably 0.001 mg to 10 mg per 1 kg of patient body weight. An effective dose for the patient is determined considering various factors, such as, age, weight, health conditions, sex, severity of disease, diet, and excretion rate. Based on these factors, one of ordinary skill in the art could determine an optimal effective dose of the composition of the present invention depending on a particular use thereof. The pharmaceutical composition is not particularly limited to the type of the formulation, route of administration, and administration method so long as the effect of the present invention can be shown.

The composition of the present invention may be administered to mammals including humans by all methods. For example, the composition of the present invention may be administered orally or parentally. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration.

The pharmaceutical composition of the present invention may be formulated as a preparation for oral or parental administration according to the route of administration as described above.

For preparations for oral administration, the composition of the present invention may be formulated in forms of a powder, granules, a tablet, a pill, a sugar tablet, a capsule, a liquid, a gel, a syrup, a slurry, and a suspension, by the methods known in the art. For preparations for parental administration, the composition of the present invention may be formulated in forms of an injection, a cream, a lotion, an external ointment, an oil, a moisturizer, a gel, an aerosol, and a nasal inhaler, by the method known in the art. These preparations are described in the literature, which is a formulary generally known in pharmaceutical chemistry (Remington's Pharmaceutical Science, 15th Edition, 1975. Mack Publishing Company, Easton, Pa. 18042, Chapter 87: Blaug, Seymour).

The pharmaceutical composition of the present invention may be used alone or in combination with other methods employing surgery, hormone treatment, chemical treatment, and biological response controller, for prevention or treatment of interleukin-4-mediated diseases.

As set forth above, the present invention provides a fusion polypeptide in which a polypeptide fragment may include 5 to 30 amino acids is fused between the first and the fifth amino acids of the fourth loop of a human-derived ferritin monomer. The fusion polypeptide of the present invention forms a protein cage, thereby sealing an effective material therein and enhancing the binding affinity of the polypeptide fragment to particular molecules, cells, or tissues of the polypeptide fragment, and thus the fusion polypeptide of the present invention is effective in the diagnosis of diseases and the development of therapeutic agents.

However, the following examples are merely for illustrating the present invention and are not intended to limit the scope of the present invention.

<Example 1> Preparation and Purification of Expression Vector

<1-1> Preparation of Expression Vector

In order to prepare a fusion protein in which AP1 peptide is linked to human ferritin light chain, a genetic recombination method was employed.

Specifically, in order to insert AP1 peptides between glycine and glycine and between glycine and proline of the fourth loop, BamHI and ApaI restriction sites were introduced to prepare cassettes, and AP1 peptides were inserted in the cassettes.

Here, as amino acid sequences of API peptides, two kinds of peptides, RKRLDRN (AP1S) and CRKRLDRNC (AP1L), were inserted. As the expression vector, pET28a(+), which is an expression vector of *E. coli*, was used. In order to synthesize the nucleotide sequences of the AP1 peptides, primers of table 1 were mixed at a molar ratio of 1:1, and then diluted to a final concentration of 1 pmol/ul. In addition, the mixed nucleotide sequences were incubated in a heat block at 95° C. for around 5 min, and then the temperature was slowly lowered to room temperature, thereby preparing double-strand AP1 gene. The pET28a(+) expression vector was treated with NdeI and XhoI restriction enzymes (purchased from TAKARA) at 37° C. for 2 h, followed by purification, and then the AP1 gene was allowed to bind to the expression vector using T4 DNA ligase.

TABLE 1

| Insertion position | Insertion peptide | Primer sequence | SEQ ID NO |
|---|---|---|---|
| GG cassette | AP1S | 5-gatcccgtaagcgtcttgatc ggaatggtgggcc-3 | 13 |
|  |  | 5-caccattccgatcaagacgct tacgg-3 | 14 |
| GG cassette | AP1L | 5-gatcctgccgtaagcgtcttg atcggaattgcggtgggcc-3 | 15 |
|  |  | 5-caccgcaattccgatcaagac gcttacggcag-3 | 16 |

TABLE 1-continued

| Insertion position | Insertion peptide | Primer sequence | SEQ ID NO |
|---|---|---|---|
| GP cassette | AP1S | 5-gatcccgtaagcgtcttgatc ggaatgggcc-3 | 17 |
| | | 5-cattccgatcaagacgcttac gg-3 | 18 |
| GP cassette | AP1L | 5-gatcctgccgtaagcgtcttg atcggaattgcgggcc-3 | 19 |
| | | 5-cgcaattccgatcaagacgct tacggcag-3 | 20 |

AP1 peptides, which are known to favorably bind to IL-4 receptor, were inserted between glycine and glycine and between glycine and proline of the four loop, that is, corresponding to between the fourth and the fifth α-helixes of the human ferritin light chain. The insertion position of the AP1 peptide corresponds to a portion in which the peptide protrudes outwardly when 24-mer peptide is formed, and into which the AP1 peptide is easily inserted. In addition, BamHI and ApaI restriction enzyme sites were introduced in a cassette type such that other peptides as well as AP1 peptide could be inserted (See FIG. 1).

<1-2> Vector Expression and Purification

*E. coli* cells were transformed with the prepared expression vectors to mass produce fusion proteins. Specifically, BL21 host cells were transformed with expression vectors in which AP1S and AP1 L genes were inserted in GG cassettes and expression vectors in which AP1 S and AP1L genes were inserted in GP cassettes. The cells were grown at 37° C. to an $OD_{600}$ value of 0.5, and expression was induced by 1 mM IPTG. Then, the cells were further cultured at 20° C. for 18 h, and then were harvested. The cells were disrupted using lysis buffer (50 mM Tris, 100 mM NaCl, mM EDTA, 1% tripton X-100, 1 mM PMSF, 0.5 mM DTT). Then, as for ferritin without AP1 peptide, only the lysate was used for purification, while as for ferritin with inserted AP1 peptide, cell pellets were solubilized in binding buffer (20 mM Tris, 500 mM NaCl, 5 mM imidazole) containing 8 M urea, and then the urea was slowly removed on Ni-NTA beads. The proteins were purified through refolding.

For the purification, the proteins were purely purified using affinity chromatography, and the molecular weights of the purified proteins were confirmed through modified SDA-PAGE electrophoresis. Specifically, the affinity chromatography employed Ni-NTA column, and the proteins were washed with wash buffer (20 mM Tris, 500 mM NaCl, 20 mM imidazole) after protein loading. Proteins attached on the columns were eluted using elution buffer (20 mM Tris, 150 mM NaCl, 180 mM Histidine), followed by electrophoresis.

As shown in FIG. 2, the SDS-PAGE results verified that about 23 kDa proteins were purified.

Example 2

Cage Formation Test of AP1 Peptide-Inserted Ferritins

<2-1> Ferritin Protein Formation Test Using Fast Protein Liquid Chromatography (FPLC)

In order to investigate whether AP1 peptide-inserted ferritin proteins form cage protein like its wild type, FPLC was carried out.

For FPLC, Superdex 200 10/300 GL column (GE Healthcare) was used, while the injection volume was 50 ul, and the buffer was 20 mM Tris-HCl (8.0), 150 mM NaCl, and 180 mM Histidine. In order to make the standard curve, wild-type ferritin (molecular weight 440 kDa), BSA (molecular weight 67 kDa), ovalbumin (45 kDa), Chymotrypsin A (25 kDa), and ribonuclease A (13 kDa) were used.

As shown in FIG. 3, the results verified that all four kinds of proteins favorably formed cages. The AP1-inserted ferritins are shown to have a smaller size than their wild type, but the formation of peaks was confirmed between 10 ml and 11 ml in an elution volume.

>2-2> Biological Transmission Electron Microscope

In order to investigate whether AP1 peptide-inserted ferritins favorably form cages, biological transmission electron microscope imaging was conducted. Each sample was made to 0.1 mg/ml, and was imaged by Korea Basic Science Institute (KBSI). Samples were negatively stained with uranyl acetate, and imaged by FEI Tecnai.

The results verified that the AP1-inserted ferritins favorably formed cages like their wild type, which were the same as the FPLC results (See FIG. 4).

<Example 3> Cell Binding Test

<3-1> Cell Binding Test Using Flow Cytometry (FACS)

In order to investigate whether AP1 peptide-inserted ferritins bind to IL-4 receptor, A549 cells overexpressing IL-4 receptor were used.

First, A549 cells were grown to about 80% confluence in a 100 mm-diameter plate. The plated cells were washed twice with PBS, and detached from the plate using Trypsin/EDTA. Then, $2\times10^5$/100 μl cells were suspended in PBS containing 1% bovine serum albumin (BSA), and incubated at 4° C. for 30 min. The human IL-4 Rα antibody (MAB230) was diluted to 1:1000 in PBS buffer containing 1% BSA, and incubated at 4° C. for 1 h, thereby blocking IL-4 receptor. The above blocking procedure was performed on one group, and was not performed on the other group, and the following experiment was performed on both groups. After washing twice with PBS, the ferritin without AP1 insertion and the AP1-inserted ferritin were diluted to 400 nM in buffer (20 mM Tris, 150 mM NaCl, 180 mM Histidine), and then allowed to bind at 4° C. for 20 min. After washing twice with PBS, the ferritin light chain antibody (D-18, sc-14420) was diluted to 1:400 in PBS buffer containing 1% BSA, and incubated in ice for 30 min. After washing twice with PBS, Alexa Fluor 488 donkey anti-goat IgG (H+L) antibody (invitrogen, USA) was diluted to 1:200 in PBS containing 1% BSA, and incubated in ice for 30 min. After washing twice with PBS, the cells were suspended in 500 ul PBS, and analyzed with FACS.

As shown in FIG. 5, the test results verified that all four kinds of AP1-inserted ferritins favorably bound to IL-4 receptor, whereas the wild type ferritin did not bind to IL-4 receptor in A549 cells overexpressing IL-4 receptor. When the IL-4 receptor was blocked using IL-4 receptor antibody and biding test was carried out, all four kinds of AP1-inserted ferritins had decreased binding levels. This means that the AP1-inserted ferritins specifically bind to the IL-4 receptor.

3-2> Cell Binding Test Using Confocal Microscope

In order to investigate whether the AP1 peptide-inserted ferritins bind to IL-4 receptor, A549 cells overexpressing IL-4 receptor were tested using confocal microscopy.

First, A549 cells were grown to about 80% confluence in a 100 mm-diameter plate. The plated cells were washed twice with PBS, and detached from the plate using Trypsin/EDTA. Then, $2\times10^5$/100 ul cells were suspended in PBS containing 1% bovine serum albumin (BSA), and incubated at 4° C. for 30 min. After washing twice with PBS, the ferritin without AP1 insertion and the AP1-inserted ferritin were diluted to 400 nM in buffer (20 mM Tris, 150 mM NaCl, 180 mM Histidine), and then allowed to bind at 4° C. for 20 min. After washing twice with PBS, the ferritin light chain antibody (D-18, sc-14420) was diluted to 1:400 in PBS buffer containing 1% BSA, and incubated in ice for 30 min. After washing twice with PBS, Alexa Fluor 488 donkey anti-goat IgG (H+L) antibody was diluted to 1:200 in PBS containing 1% BSA, and then incubated in ice for 30 min. After washing twice with PBS, 4% paraformaldehyde (PFA) was added for cell fixation, and cells in suspension were added in the 8-well slide chamber. The cells were attached in the chamber by centrifugation at 1000 rpm for 10 min.

After washing twice with PBS, the cells were stained by incubation with 4',6-diamidino-2-phenylindole (DAPI) for 3 min in dark place, mounted in antifade reagent to close a cover glass, and analyzed by Z-stack type confocal microscopy.

Like the FACS results, it was verified that the wild type did not bind to A549 cells, whereas all four kinds of AP1-inserted ferritins favorably bound to the cell membrane (FIG. 6).

<Example 4> Receptor-Mediated Endocytosis

In order to investigate whether AP1 peptide-inserted ferritins show a favorable uptake into cells through IL-4 receptor expressed in A549 cells, the present test was carried out.

A549 cells were seeded in 8-well slide chamber at $1 \times 10^4$/200 ul, and allowed to adhere to chamber overnight. After washing twice with PBS, the ferritin without AP1 insertion and the AP1-inserted ferritin were diluted to 400 nM in buffer (20 mM Tris, 150 mM NaCl, 180 mM Histidine), and then allowed to bind at 37° C. for 1 h. After washing twice with PBS, the cells were incubated in cold methanol at 20° C. for 20 min for membrane permeability. After washing twice with PBS, PBS containing 1% BSA was added, followed by blocking at room temperature for 30 min. After washing twice with PBS, anti-His-probe (H-15) Alexa Fluor 647 antibody was diluted to 1:40 in PBS, and incubated at 4° C. overnight. After washing twice with PBS, the cells were stained by incubation with DAPI for 3 min in dark place, mounted in antifade reagent to close a cover glass, and analyzed by confocal microscopy.

As shown in FIG. 7, the results verified the uptake of four kinds of AP1-inserted ferritins into cytosol in cells.

<Example 5> Binding Affinity Analysis of Active Polypeptide

<5-1> Surface Plasmon Resonance (SPR) Analysis

For analysis, 50 ul of 200 mM sodium acetate (NaOAC, pH 4.0) was added to 50 ul of 0.74 mg/ml IL-4 receptor protein, followed by mixing, and then $H_2O$ was added such that 20 mM sodium acetate buffer had a total volume of 500 ul.

Then, 40 mM N-(3-dimethylaminopropyl)-N'-ethylcarbodiimide hydrochloride (EDC)/10 mM N-hydroxy-succinimide (NHS) were allowed to flow over each channel (left, right) of carboxymethyl dextran chip for 7 min for surface activation, and then 200 ul of the prepared IL-4 receptor protein was allowed to flow over the left channel for 7 min for immobilization. Here, the right channel was used as a reference channel. In the two channels, left channel and right channel, 1M ethanolamine (pH 8.5) solution was allowed to flow over the unreacted surface for 7 min for blocking, so as to reduce non-specific adsorption thereof. All test procedures were conducted at a temperature of 25° C. and the flow rate was 25 ul/min.

The buffer (20 mM Tris-HCl pH 8.0, 150 mM NaCl, 180 mM Histidine, 62.5 ug/ml BSA, 0.005% Tween 20) was used through filtering and degassing. The wild type ferritin and the AP1-inserted ferritins were allowed to flow over at concentrations of 0.65 nM, 1.3 nM, 2.6 nM, 5.2 nM, 10.4 nM, 20.8 nM, and 41.6 nM for 3 min, and the same buffer was allowed to flow over for 3 min. For regeneration, 2 M NaCl was allowed to flow over for 1 h to wash the proteins remaining without dissociation. Specific binding values, obtained by subtracting the right channel value from the left channel value, in the concentration ranging from 0.65 nM to 10.4 nM, were plotted on a graph.

Figure 8:
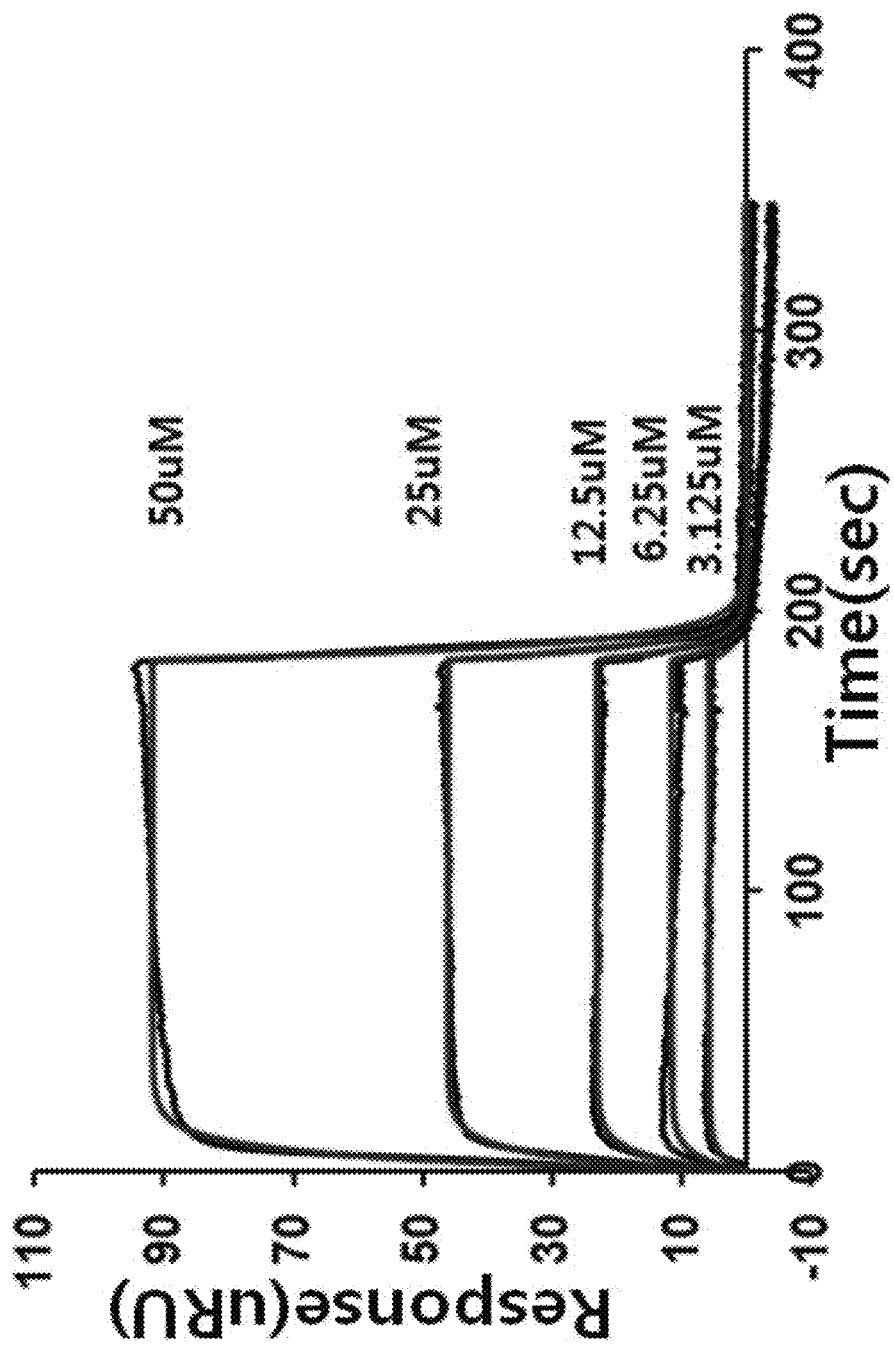
FIG. 8 is a graph showing surface plasmon resonance analysis results for measuring binding affinity between AP1 peptide and IL-4 receptor.

In order to obtain the Kd value of AP1 peptide and IL-4R, the buffer of 10 mM Hepes pH 8.4, 150 mM NaCl, 3.4 mM EDTA, 62.5 ug/ml BSA, and 0.005% Tween 20 was used through filtering and degasing. AP1 peptide was allowed to flow over at concentrations of 3.125 uM, 6.25 uM, 12.5 uM, 25 uM, and 50 uM for 3 min, and the same buffer was allowed to flow over for 3 min. For regeneration, 2 M NaCl was allowed to flow over for 1 min to wash the proteins remaining without dissociation. Specific binding values, obtained by subtracting the right channel value from the left channel value, in the respective concentrations, were plotted on a graph (see FIG. 8).

In the binding graph, the RU value expressing the amount of bound protein was measured by subtracting the blank (buffer) value and reference channel (right channel) value, using Scrubber software. The $K_D$ value was obtained from the binding RU (Req) values measured at the respective concentrations using KaleidaGraph software. Here, the $K_D$ value was obtained by measuring the association phase value for sufficient time for the R values of the association phase to reach near equilibrium values (Req) to plot five or more different concentrations of each protein within a 10-fold range of $K_D$ and Req measured in SPR and then performing curve fitting using equation, m1/(1+m2/m0); m1=1; m2=1 (m1; Vmax, m2; Kd).

It has been known in the precedent paper that the $K_D$ value of IL-4 and IL-4 receptor was about $3.82 \times 10^{-10}$ (Andrews A L, Holloway J W, Holgate S T, Davies D E. J Immunol. 2006 Jun. 15; 176(12):7456-7461).

The $K_D$ value of AP1 peptide and IL-4 receptor was calculated from the measured binding RU values for different concentrations of AP1, and as a result, the $K_D$ value was calculated as $5.54 \times 10^{-3}$.

TABLE 2

$K_D$ (equilibrium constant) value of IL4R, AP-1, and fusion polypeptide of present invention

| | IL-4R | $K_D$(M) |
|---|---|---|
| | IL-4 | $3.82 \times 10^{-10}$ |
| | AP-1 peptide | $5.54 \times 10^{-3}$ |
| FTL | GG-AP1S | $1.19 \times 10^{-9}$ |
| | GP-AP1S | $4.29 \times 10^{-9}$ |
| | GG-AP1L | $25.9 \times 10^{-9}$ |
| | GP-AP1L | $9.9 \times 10^{-9}$ |

On the contrary, $K_D$ values of AP1-inserted ferritins were calculated as shown in table 2 above. It can be seen that the affinity to IL-4 receptor was $10^5$-$10^6$ times more enhanced in the AP1-inserted ferritins than in AP1 peptide. There were differences in the binding peak among four kinds of AP1-inserted ferritin mutants, and thus it can be seen that association and dissociation patterns are different between AP1-S-inserted ferritins and AP1-L-inserted ferritins. AP1-S ferritins without cysteins at both sides had fast association (Ka) and dissociation (Kd), and showed the binding while saturation occurs in a concentration-dependent manner. However, AP1-L ferritins with cysteins at both sides had association and dissociation patterns, which were not significantly different from those of AP1-L ferritins, at lower concentrations, and the binding of AP1-L ferritins was not significantly different from that of AP1-S ferritins. RU values were not different between the two, but the higher concentration resulted in a higher RU value, more binding, and slower dissociation (FIG. 9).

<5-2> Binding Affinity Analysis Depending on Concentration (SPR Analysis)

In order to compare the binding degrees of four kinds of AP1-inserted ferritin mutants to IL-4 receptor, SPR analysis was carried out. The experiment was conducted like in example <5-1>, and RU values shown for concentrations ranging from 0.65 nM to 41.6 nM were plotted on a graph using GraphPad prism 4 program.

Figure 10:
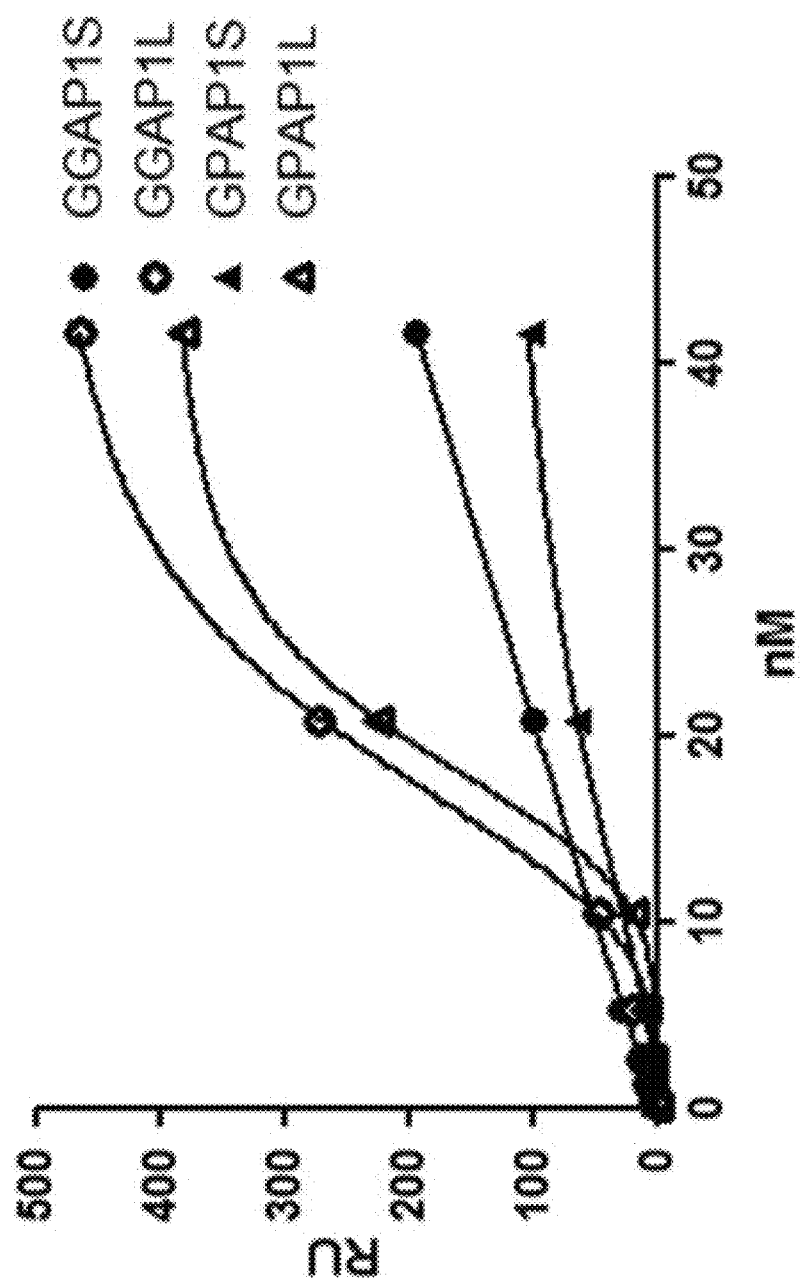
FIG. 10 is a graphing showing surface plasmon resonance analysis results for different concentrations for measuring binding affinity of four kinds of AP1 peptide-inserted ferritins to IL-4 receptor.
Figure 11A:
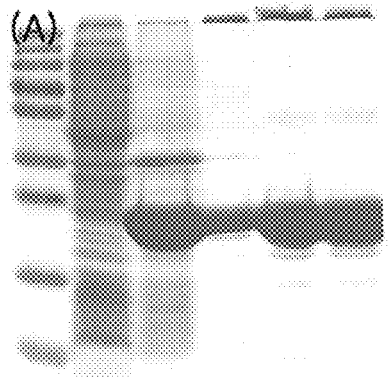
FIG. 11A is an SDS-PAGE result image of FTL-AP1_RGD (lane 1; marker, lane 2; lysate supernatant, lane 3; lysate pellet, lane 4; Elute fraction 2, lane 5; Elute fraction 3, lane 6; Elute fraction 4).
Figure 11B:
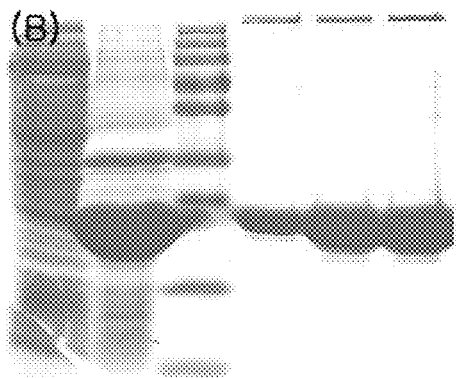
FIG. 11B is an SDS-PAGE result image of FTL-AP1-GRGDSP (lane 1; lysate supernatant, lane 2; lysate pellet, lane 3; marker, lane 4; Elute fraction 2, lane 5; Elute fraction 3, lane 6; Elute fraction 4).
Figure 11C:
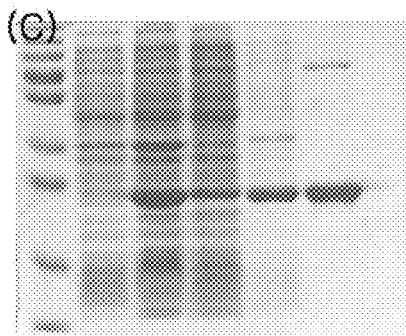
FIG. 11C is an SDS-PAGE result image of FTL-RGD_AP1 (lane 1; marker, lane 2; uninduced lysate, lane 3; induced lysate, lane 4; lysate supernatant, lane 5; pellet urea extraction, lane 6; Elute fraction).
Figure 11D:
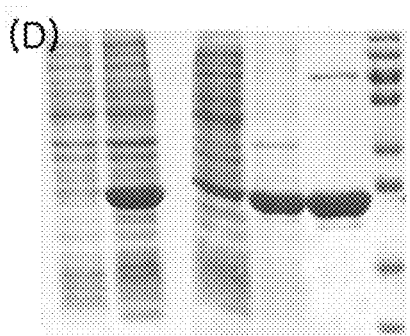
FIG. 11D is an SDS-PAGE result image of FTL-GRGD-SP_AP1 (lane 1; uninduced lysate, lane 2; induced lysate, lane 3; lysate supernatant, lane 4; pellet urea extraction, lane 5; Elute fraction, lane 6; Marker).
Figure 11E:
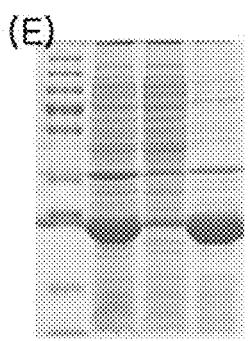
FIG. 11E is an SDS-PAGE result image of FTL-AP1_AP1 (lane 1; marker, lane 2; induced lysate, lane 3; lysate supernatant, lane 4; lysate pellet).
Figure 11F:
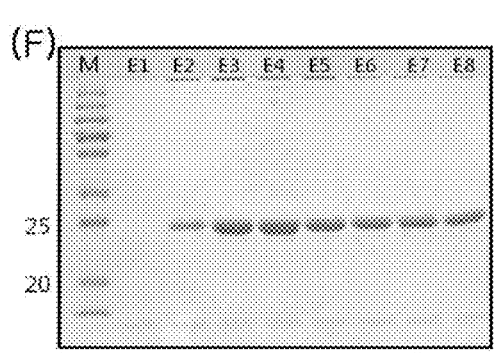
FIG. 11F is an SDS-PAGE result image=of SDS-PAGE confirming expression of FTL-AP1_AP1 peptide (M: Size marker, E2-E8: lanes loading separated and purified FTL-AP1_AP1 peptides).
Figure 12A:
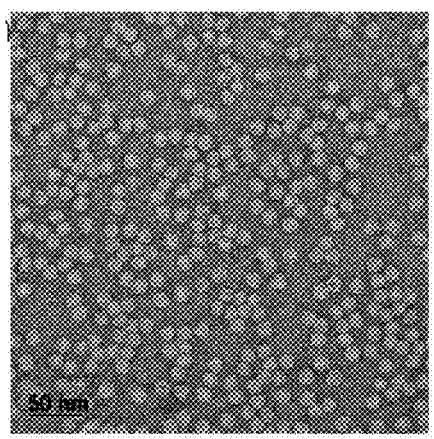
FIG. 12A is a biological electron microscopic image confirming the cage formation of FTL-AP1_GRD.
Figure 12B:
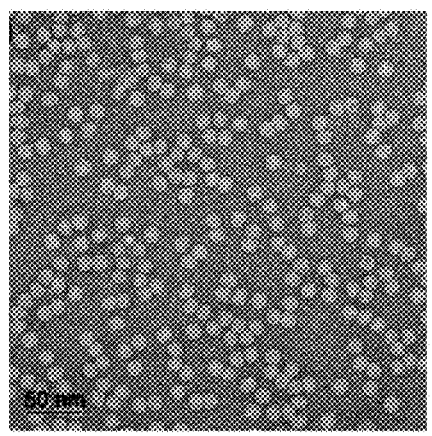
FIG. 12B is a biological electron microscopic image confirming the cage formation of FTL-AP1_GRGDSP.
Figure 12C:
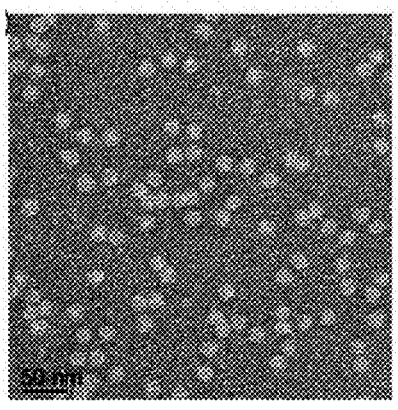
FIG. 12C is a biological electron microscopic image confirming the cage formation of FTL-AP1_AP1.
Figure 12D:
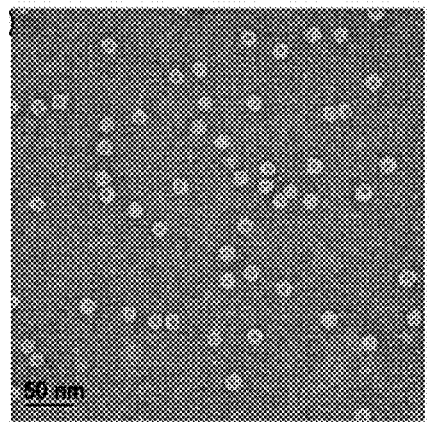
FIG. 12D is a biological electron microscopic image confirming the cage formation of FTL-AP1_AP1.

As a result, it can be seen that the AP1S-inserted ferritins showed an addictive increase in RU values with increased concentration, while the AP1L-inserted ferritins showed a significant increase in RU values with increased concentration. It can be confirmed that the increase in RU values with increased concentration was significantly larger in the AP1L-inserted ferritins than in AP1S-inserted ferritins (See FIG. 10).

<Example 6> Preparation and Purification of Expression Vector for Preparing Ferritin in which Second Polypeptide Fragment is Fused to N-Terminal Thereof <6-1> Preparation of Expression Vector AP1 peptide was additionally inserted in the fusion polypeptide prepared in Example 1. A fusion polypeptide (FTL-AP1 AP1) in which AP1 peptides were inserted to two sides of one ferritin monomer was constructed by additionally inserting AP1 peptide to the N-terminal of the clone in which AP1 peptide (short form, AP1S) was inserted between glycine and glycine (GG cassette) of the fourth loop, that is, between the fourth α-helix and the fifth α-helix of the human ferritin light chain.

The used polypeptide was a fusion polypeptide (FTL GG-AP1S) in which AP1S has been folded in GG cassette, and was named FTL-AP1 in the Example. The amino acid sequence of the additionally inserted AP1 was RKRLDRN as AP1S, and the insertion position was the N-terminal of the fusion polypeptide. In the Example, the fusion polypeptide in which AP1S was fused to N-terminal of FTL_GG-AP1S (FTL-AP1) was named FTL-AP1_AP1.

In addition, a fusion polypeptide in which AP1 peptide and RGD peptide were linked to the human ferritin light chain was prepared.

A fusion polypeptide (FTL-AP1_RGD) in which AP1 peptide and RGD peptide were inserted in one ferritin monomer was constructed by inserting AP1 peptide to the N-terminal of the clone in which RGD peptide was inserted between glycine and glycine (GG cassette) of the fourth loop region, that is, between the fourth α-helix and the fifth α-helix of the human ferritin light chain. Here, a fusion α-polypeptide (FTL-RGD-AP1) was constructed when AP1 peptide was exchanged with RGD peptide.

The gene of the fusion protein of the present invention was amplified through PCR (denaturation 95° C. (30 sec), annealing temp. 60° C. (30 sec), extension temp. 72° C. (1 min), 35 cycles) using a forward primer having the AP1 peptide sequence and the linker sequence (GGGSG) and a reverse primer having FTL sequence, as shown in table 3 below, and using FTL_GG-AP1S construct as a template. The size of the PCR amplification product was checked through agarose gel electrophoresis, followed by gel extraction. Thereafter, the amplified gene was treated with NdeI and XhoI (purchased from TAKARA) at 37° C. for 2 h. Also, pET28a(+) expression vector was treated with the same restriction enzymes, followed by purification, and then the gene was ligated to the expression vector using T4 DNA ligase. The insertion of the gene was validated through sequencing.

TABLE 3

Primer combination for FTL-AP1_AP1 preparation

| Primer | Primer sequence | SEQ ID NO |
|---|---|---|
| Forward primer | 5-GGGCATATGCGTAAGCGTCTTGATCGGAATG GAGGAGGAAGTGGAATGAGCTCCCAGATTCGTC AG-3 | 21 |
| Reverse primer | 5-GCTCGAGTTAGTCGTGCTTGAGAGTGAGC-3 | 22 |

<6-2> Vector Expression and Purification

E. coli cells were transformed with the prepared expression vectors to mass produce fusion proteins. BL21 host cells were transformed with expression vectors in which FTL-RGD_AP1, FTL-GRGDSP-AP1, FTL-AP1-RGD, FTL-AP1-GRGDSP, and FTL-AP1-AP1 were inserted, respectively. The cells were grown in LB media at 37° C. to an $OD_{600}$ value of 0.5, and expression was induced by 1 mM IPTG. Then, the cells were further cultured at 20° C. for 18 h, and then were harvested. The cells were disrupted using lysis buffer (50 mM Tris, 100 mM NaCl, 1 mM EDTA, 1% tripton X-100, 1 mM PMSF, 0.5 mM DTT). Then, cell pellets were solubilized in binding buffer (20 mM Tris, 500 mM NaCl, 5 mM imidazole) containing 8 M urea. Afterwards, the urea was slowly removed on Ni-NTA beads, and the protein was purified through refolding.

For the purification, the proteins were purely purified using affinity chromatography, and the molecular weights of the purified proteins were confirmed through modified SDA-PAGE electrophoresis. Specifically, the affinity chromatography employed Ni-NTA column, and the proteins were washed with wash buffer (20 mM Tris, 500 mM NaCl, 20 mM imidazole) after protein loading. Proteins attached on the columns were eluted using elution buffer (20 mM Tris, 150 mM NaCl, 180 mM Histidine), followed by electrophoresis.

As shown in FIG. 11, the SDS-PAGE results verified that about 23 kDa proteins were purified.

<Example 7> Cage Formation Test of Peptide-Inserted Ferritins

<7-1> Ferritin Protein Formation Test Using Fast Protein Liquid Chromatography (FPLC)

FPLC was carried out by the same method as in example <2-1>.

Figure 15:
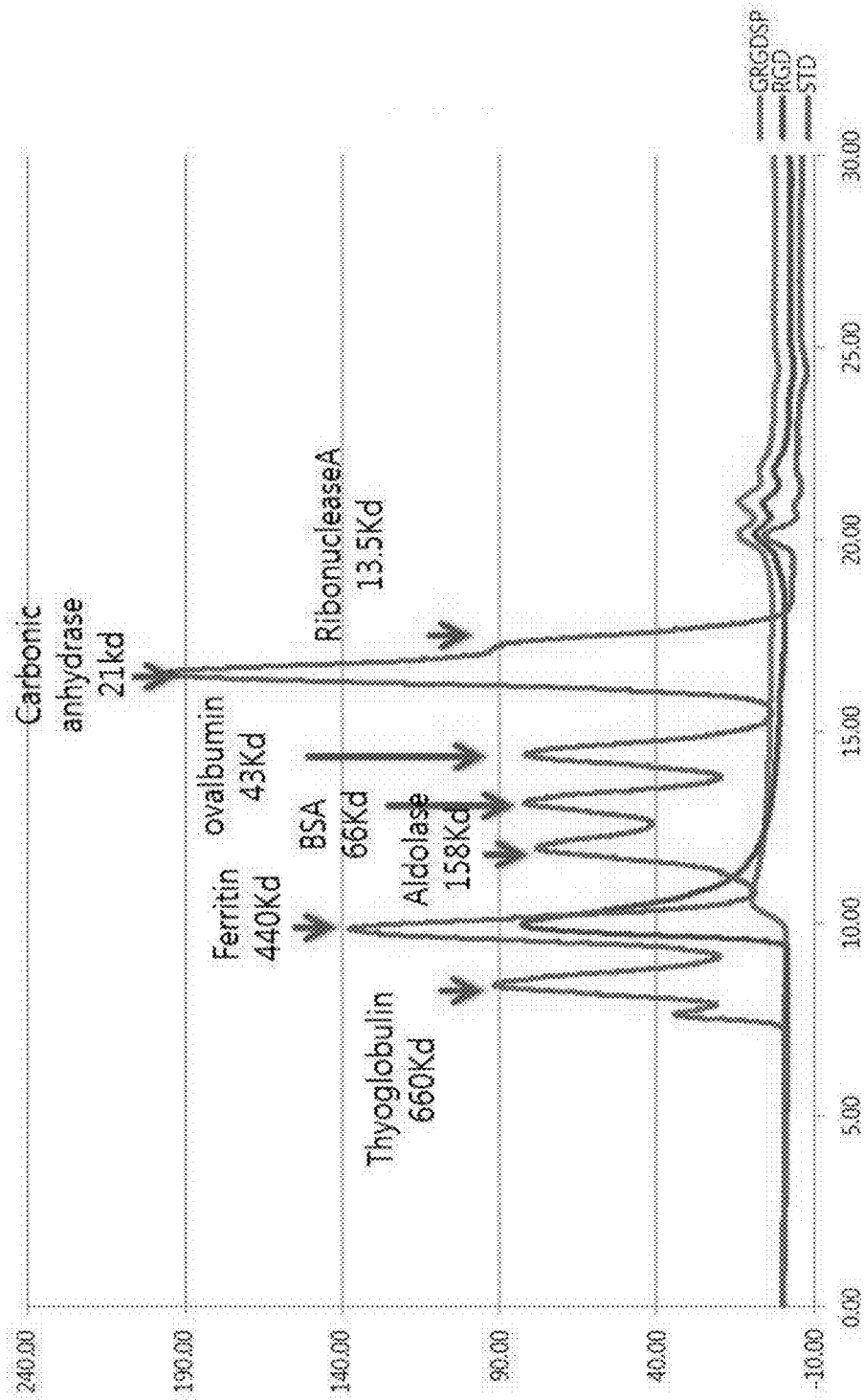
FIG. 15 is a graph that shows fast protein liquid chromatography (FPLC) results of expressed fusion proteins (Y axis: absorbance (mRU) at 280 nm, X axis: elution volume (ml), GRGDSP: FTL-AP1_GRGDSP ferritin having inserted AP1 and GRGDSP, RGD: FTL-AP1_RGD ferritin having inserted AP1 and RGD, STD: Standard).

As shown in FIG. 15, the results confirmed that both FTL-AP1-RGD and FTL-AP1-GRGDSP, in which peptides were inserted, favorably formed cages. The peptide-inserted ferritins are shown to have a smaller size than the wild type, but the formation of peaks was confirmed between 10 ml and 11 ml in an elution volume.

<7-2> Biological Transmission Electron Microscope

In order to investigate whether peptide-inserted ferritins favorably form cages, biological transmission electron microscopy imaging was conducted.

The concentration of each sample was 0.2 mg/ml, and the samples were imaged employing the same method as in Example <2-2> by the Korea Basic Science Institute (KBSI).

The results verified that the peptide-inserted ferritins favorably formed cages like the wild type, which were the same as the FPLC results (See FIG. 12).

<Example 8> Cell Binding Test Using FACS

In order to investigate whether the ferritin in which AP1 peptides have been inserted to two sites (FTL-AP1_AP1) favorably binds to IL-4 receptor, the cell binding test was conducted by the same method as in example <3-1> using A549 cells overexpressing IL-4 receptor.

First, A549 cells were grown to about 80% confluence in a 100 φ plate. The plated cells were washed twice with PBS, and detached from the plate using Trypsin/EDTA. Then, $2 \times 10^5/100$ ul cells were suspended in PBS containing 1% bovine serum albumin (BSA), and incubated at 4° C. for 30 min. After washing twice with PBS, FTL-AP1 and FTL-AP1 AP1 were diluted to 400 nM, 200 nM and 40 nM in buffer (20 mM Tris, 150 mM NaCl, 180 mM Histidine), and then allowed to bind at 4° C. for 20 min. After washing twice with PBS, the ferritin light chain antibody (D-18, sc-14420) was diluted to 1:400 in PBS buffer containing 1% BSA, and incubated in ice for 30 min. After washing twice with PBS, Alexa Fluor 488 donkey anti-goat IgG (H+L) antibody was diluted to 1:200 in PBS containing 1% BSA, and then incubated in ice for 30 min. After washing twice with PBS, the cells were suspended in 500 ul PBS, and then analyzed with FACS.

Figure 13:
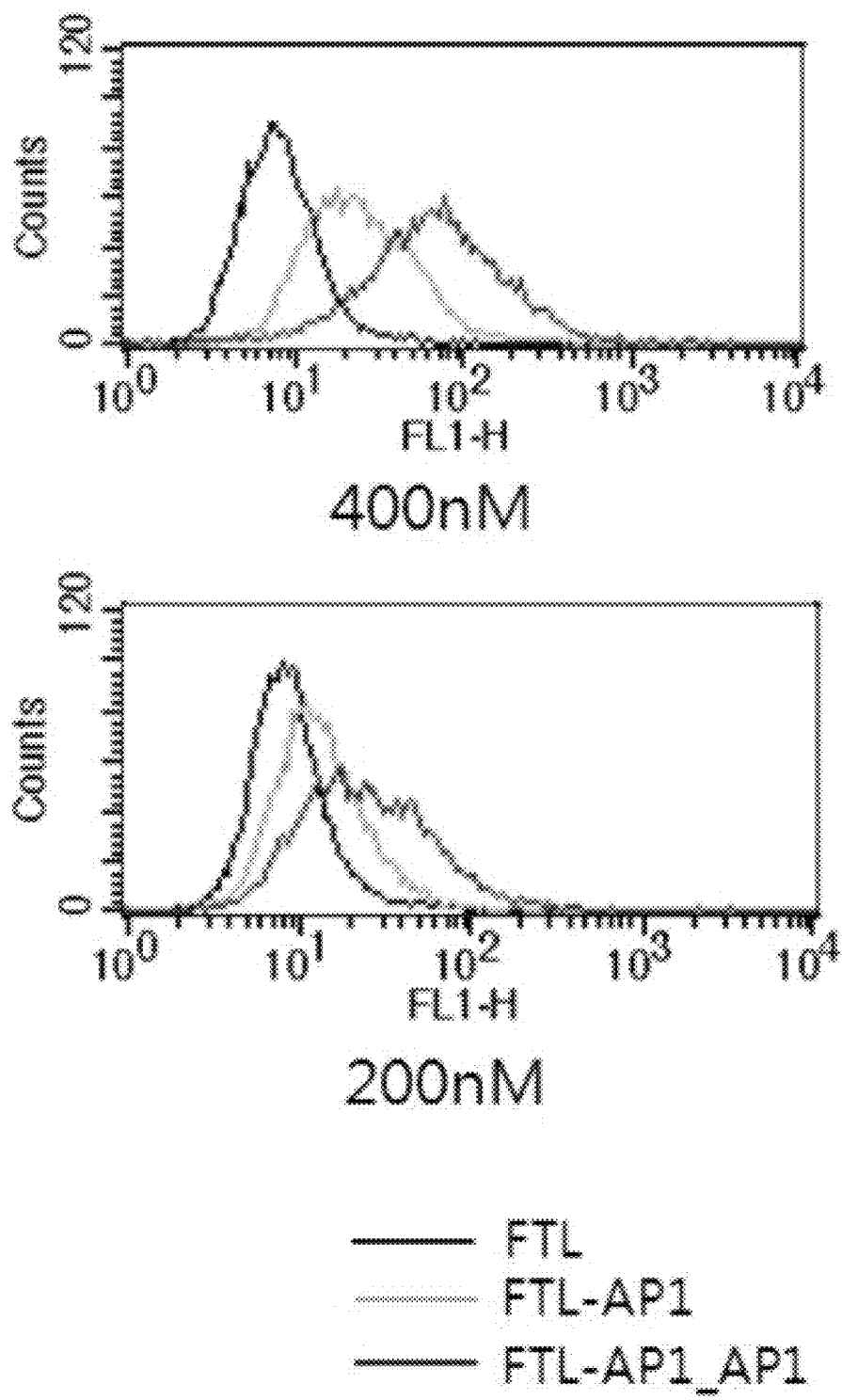
FIG. 13 are graphs that show a cell binding test result graph using FACS (FTL (dark line): ferritin without AP1 peptide insertion, FTL-AP1 (light gray line): ferritin having one inserted AP1 peptide, FTL-AP1_AP1 (semi-dark line): ferritin having two inserted AP1 peptides, FL1-H: the fluorescence intensity per cell, counts: cell count).

As shown in FIG. 13, the test results verified that FTL-AP1_AP1 further bound to IL-4 receptor in larger amount than FTL-AP1 at 400 nM and 200 nM.

<Example 9> Surface Plasmon Resonance (SPR) Analysis

<9-1> Analysis on Binding Affinity of RGD and AP1 Peptides-Inserted Human Ferritin to Integrin Alphavbeta3

For analysis, 35 ul of 200 mM sodium acetate (NaOAC, pH 4.0) was added to 35 ul of 0.25 mg/ml alphavbeta3 protein, followed by mixing, and then H$_2$O was added such that 20 mM sodium acetate buffer had a total volume of 350 ul.

Then, 40 mM N-(3-dimethylaminopropyl)-N'-ethylcarbodiimide hydrochloride (EDC)/10 mM N-hydroxy-succinimide (NHS) were allowed to flow over each channel (left, right) of carboxymethyl dextran chip for 7 min for surface activation, and then 200 ul of the prepared alphavbeta3 protein was allowed to flow over the left channel for 7 min for immobilization. Here, the right channel was used as a reference channel. In the two channels, left channel and right channel, 1M ethanolamine (pH 8.5) solution was allowed to flow over the unreacted surface for 7 min for blocking, so as to reduce non-specific adsorption thereof. All test procedures were conducted at a temperature of 25° C. and the flow rate was 25 ul/min.

The buffer (10 mM Hepes pH 7.4, 150 mM NaCl, 180 mM Histidine, 1 mM MgCl$_2$, 0.005% Tween 20) was used through filtering and degassing. The wild type ferritin and the RGD-inserted ferritins were allowed to flow over at concentrations of 0.65 nM, 1.3 nM, 2.6 nM, 5.2 nM, 10.4 nM, 20.8 nM, and 41.6 nM, respectively, for 3 min, and the same buffer was allowed to flow over for 3 min. For regeneration, 2 M NaCl was allowed to flow over for 1 min to wash the proteins remaining without dissociation. Specific binding values, obtained by subtracting the right channel value from the left channel value, in the concentration ranging from 0.65 nM to 10.4 nM, were plotted on a graph.

In the binding graph, the RU value expressing the amount of bound protein was measured by subtracting the blank (buffer) value and reference channel (right channel) value, using Scrubber software.

The $K_D$ value of RGD-inserted ferritin and alphavbeta3 was calculated from the measured binding RU values for different concentrations of RGD-inserted ferritin, and as a result, the $K_D$ value was $6.86 \times 10^{-8}$.

Figure 16:
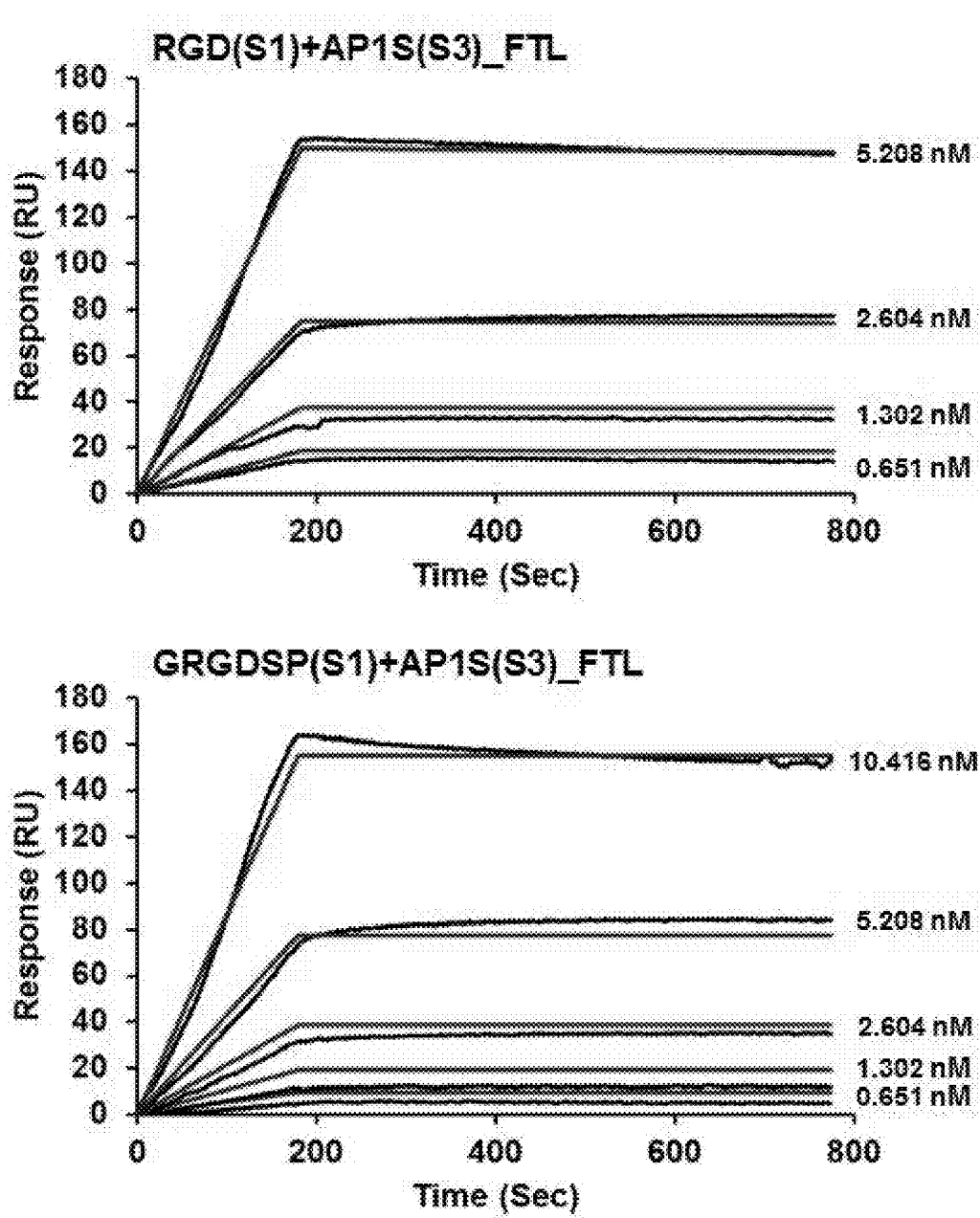
FIG. 16 are graphs that show surface plasmon resonance (SPR) analysis results of binding affinity between integrin alphavbeta3 and RGD peptide-inserted ferritin (RGD(S1)+AP1S(S3) FTL: ferritin having inserted RGD and AP1 peptides, GRGDSP(S1)+AP1S(S3) FTL: ferritin having inserted GRGDSP and AP1 peptides).

As shown in FIG. 16, the test results verified that FTL-RGD-AP1 and FTL-GRGDSP-AP1 bound to integrin alphavbeta3 in a concentration-dependent manner.

<9-2> Comparison of FTL-AP1 AP1 Binding Affinity

For comparison of binding affinity between FTL-AP1 and FTL-AP1_AP1, surface plasmon resonance analysis was conducted. Analysis was conducted by the same method as in Example <5-1>. The binding of FTL-AP1 was analyzed at concentrations of 0.26 nM, 1.041 nM, 2.083 nM, and 4.166 nM, respectively, and the binding of FTL-AP1_AP1 was analyzed at concentrations of 0.520 nM, 1.041 nM, 2.083 nM, and 4.166 nM, respectively.

Figure 14:
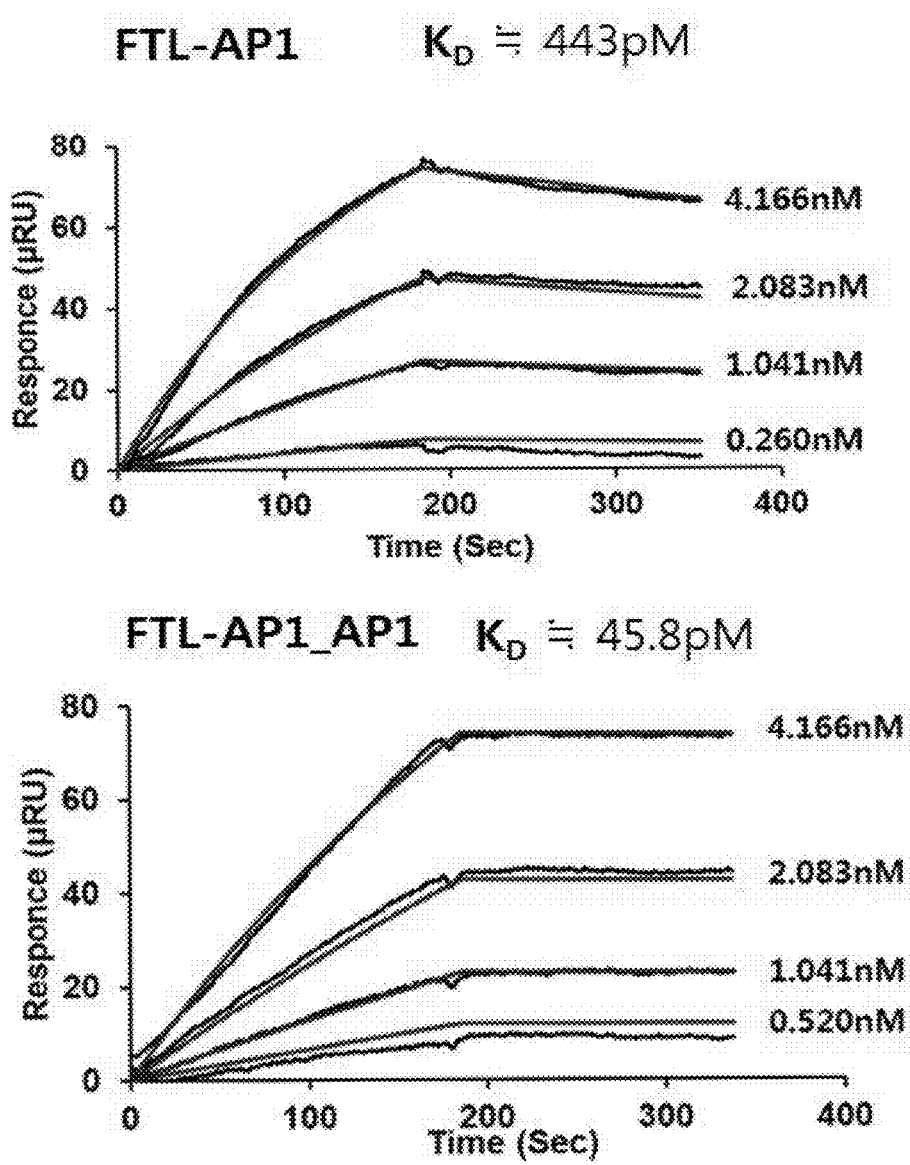
FIG. 14 are graphes that show surface plasmon resonance (SPR) analysis results for binding affinity comparison between FTL-AP1 and FTL-AP1_AP1 (FTL-AP1: binding affinity analysis results between ferritin having one inserted AP1 peptide and IL-4 receptor, FTL-AP1_AP1: binding affinity analysis results between ferritin having two inserted AP1 peptides and IL-4 receptor).

As shown in FIG. 14 and Table 4, the test results verified that the $K_D$ value of FTL-AP1 was 443 pM, while the $K_D$ value of FTL-AP1_AP1 was 45.8 pM. Thus, the binding affinity of FTL-AP1_AP1 was 10 times enhanced compared with that of FTL-AP1.

TABLE 4

| Ligand | Kon (M$^{-1}$S$^{-1}$) | Koff (S$^{-1}$) | K$_D$ (M$^{-1}$) |
|---|---|---|---|
| FTL-AP1 | 1.22 ± 0.64 × 10$^6$ | 1.25 ± 0.4 × 10$^{-3}$ | 1.44 ± 0.9 × 10$^{-9}$ |
| FTL-AP1-AP1 | 8.26 × 10$^5$ | 3.8 × 10$^{-5}$ | 4.58 × 10$^{-11}$ |

<Example 10> Test on Effective Material Transfer

In order to verify the drug delivery effect of ferritin-derived fusion polypeptide of the present invention, it was investigated whether AP1 peptide inserted in the ferritin cage has an effect on asthma.

<10-1> Preparation of Animal Model of Asthma

Wild-type C57BL/6J mice were purchased from Jackson Laboratory (Bar Harbor, Me., USA), and bred in a pathogen-free animal facility. All animals were fed with a normal diet (PMI Lab Diet) with free access to water. 6-8-week-old female mice were used for this study. Animal care and experimental procedures were performed with the approval of the Animal Care Committee of KAIST.

Asthma induction was performed by the existing method (Corry D B, Folkesson H G, Warnock M L, Erle D J, Matthay M A, et al. (1996) J Exp Med 183: 109117).

Briefly, *Aspergillus oryzae* protease (1 mg/mL in PBS, Sigma-Aldrich) and chicken egg ovalbumin (OVA, 0.5 mg/mL in PBS, Sigma-Aldrich) allergen (APO) were mixed 1:9 (v/v) immediately before administration. Mice received four intraperitoneal sensitizations and the intranasal challenge every 4 days (0, 4, 8, 12, 16) with 50 uL of allergen. For intranasal challenge, mice were lightly anesthetized with isoflurane inhalation (Abbott Laboratory, Abbott Park, Ill., USA). A 50 uL of AP1-retaining ferritin cage (GG-AP1L, 157cysAP1-PBNC) or AP1-not-inserted ferritin cage (wt FTL), which was diluted to 1 mg/ml in PBS, was administered 1 h before allergen challenge.

<10-2> Test on Asthma Symptoms Induction

For phenotypes of allergic asthma, AHR, BAL cytology, BAL glycoprotein assay, and lung histopathology were performed by the existing method (Lee, S. H., et al. (2003) Nat. Med. 9, 128111286).

Briefly, 16 h after final intranasal challenge, AHR was measured with a FlexiVent system (SCIREQ Inc., Montreal, Canada). After anesthetization with pentobarbital sodium (Hanlim Pharma Co., Seoul, Korea, 60 mg/kg) and intubation with 20-gauge cannula, mice were connected to the FlexiVent system through the endotracheal cannula.

After paralyzation with pancuronium bromide (Sigma-Aldrich, 1 mg/kg), mice were ventilated at a respiratory rate of 150 breaths/min and tidal volume of 10 mL/kg against a positive end expiratory pressure of 3 $CmH_2O$.

To measure lung resistances, mice were given incremental doses of methacholine (Sigma-Aldrich) with an inhaler (0=normal saline only, 1, 3, 9, 18, 27 mg/mL).

<10-3> Test on Asthma Symptoms Measurement

The airway resistances were allowed to return to the baseline after each dose of methacholine.

Then, airway hyper-responsiveness (AHR), BAL cytology, and secreted glycoprotein assays were performed by the existing method (Lee, S. H. et al., (2004) J. Allergy Clin. Immunol. 113, 72778).

As shown in FIG. 17a, the measurement results confirmed that the airway hyper-responsiveness (AHR) was significantly suppressed in the group administered with AP1-containing ferritin (APO+$^{157}$cysAP1-PBNC), in comparison with the control ferritin.

In addition, it was confirmed that the count of inflammation cells in bronchoalveolar lavage (BAL) fluid, especially, eosinophils, was also significantly decreased in the group administered with AP1-containing ferritin ($^{157}$cysAP1-PBNC), in comparison with the control ferritin.

<10-4> Measurement of Secreted Glycoprotein in BAL Fluid

Levels of secreted glycoprotein were measured with modified ELISA by the existing method (Lee, S. H. et al., (2004) J. Allergy Clin. Immunol. 113, 72778.).

Briefly, mucin standard (derived from porcine stomach, Sigma-Aldrich) was diluted 2-fold serially with PBS. BAL fluid samples were also diluted 2-fold serially with PBS beginning at a 1:100 dilution.

40 ul of each sample was transferred to an ELSA plate Greiner, Kremsmunster, Austria), and incubated at 37° C. for 2 h. After incubation and washing, plates were blocked with 200 ul of 0.2% I-block (Applied Biosystems, Foster City, Calif., USA), and incubated at 37° C. for 2 h. After washing, 40 ul of biotinylated jacalin (5 ug/mL glycoprotein binding lectin, Vector Laboratories, Burlingame, Calif., USA) was added, and incubated at 4° C. overnight. The next day, after washing, alkaline phosphatase-conjugated streptavidin (1:1000 dilution, BD Biosciences) was added, and incubated at room temperature for 30 min. After final washing upon the completion of the reaction, 70 ul of alkaline phosphatase substrate (5 mmol in 0.1 mol/L alkaline buffer, Sigma-Aldrich) was added, and developed until a mucin standard curve was readily apparent. After termination of the reaction with addition of 40 ul of 0.5 N sodium hydroxide, optical density was measured at 405 nm by an ELISA reader (BioRad, Hercules, Calif., USA).

As the measurement results, the amount of secreted glycoprotein in BAL fluid was also significantly reduced in the group administered with AP1-containing ferritin ($^{157}$cysAP1-PBNC) (see FIG. 17d).

<10-5> Microstructure Observation

Finally, the experimental mice were sacrificed, and lung slide specimens stained with periodic acid Schiff (PAS) were prepared. Then, changes of inflammatory cells and goblet cells were observed (arrowhead: mucin-positive goblet cell, arrow: inflammatory cell).

As a result, the counts of peribronchial inflammatory cells (indicated by arrow) and mucus-producing goblet cells (indicated by arrowhead) were significantly reduced in the group administered with AP1-containing ferritin.

Summarizing those results, it was confirmed that the asthma symptom relieving effect was shown in the group administered with AP1-containing ferritin. This suggests that the ferritin cage effectively acts as a drug delivery system.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A fusion polypeptide, comprising a first polypeptide fragment comprising 5 to 30 amino acids, the first polypeptide fragment is fused between a first amino acid and a fifth amino acid of a fourth loop of a human-derived ferritin monomer; and
a second polypeptide fragment comprising 5 to 30 amino acids, the second polypeptide fragment is fused to an N-terminal of the human-derived ferritin monomer.

2. The fusion polypeptide of claim 1, wherein the human-derived ferritin monomer is a human-derived ferritin light chain.

3. The fusion polypeptide of claim 1, wherein the human-derived ferritin monomer is a polypeptide comprising an amino acid sequence represented by SEQ ID NO: 1.

4. A fusion polypeptide, comprising a first polypeptide fragment comprising 5 to 30 amino acids, the first polypeptide fragment is fused between a first amino acid and a fifth amino acid of a fourth loop of a human-derived ferritin monomer, wherein the first amino acid is the $154^{th}$ amino acid of an amino acid sequence represented by SEQ ID NO: 1 and the fifth amino acid is the $158^{th}$ amino acid of the amino acid sequence represented by SEQ ID NO: 1.

5. The fusion polypeptide of claim 4, wherein some of the $154^{th}$ to $158^{th}$ amino acids of the amino acid sequence represented by SEQ ID NO: 1 are removed.

6. A fusion polypeptide, comprising a first polypeptide fragment comprising 5 to 30 amino acids, the first polypeptide fragment is fused between a first amino acid and a fifth amino acid of a fourth loop of a human-derived ferritin monomer, wherein the first polypeptide fragment is represented by General Formula I below:

N terminal-X1-X2-X3-C terminal     (General formula I)

wherein:
X1 and X3 each is a linker comprising 1 to 3 amino acids; and
X2 is a polypeptide represented by a sequence selected from the group consisting of SEQ ID NOs: 6, 7, 33, and 34.

7. The fusion polypeptide of claim 6, wherein the linker is a restriction enzyme cleavage site.

8. The fusion polypeptide of claim 6, wherein X1 is glycine-serine, and X3 is glycine-proline or glycine-glycine-proline.

9. The fusion polypeptide of claim 1, wherein the fusion polypeptide comprises an amino acid sequence selected from the group consisting of SEQ ID NOs: 2 to 5.

10. The fusion polypeptide of claim 1, wherein the fusion polypeptide comprises an amino acid sequence selected from the group consisting of SEQ ID NOs: 23, 25, 27, 29, and 31.

11. The fusion polypeptide of claim 1, wherein at least one of the first polypeptide fragment and the second polypeptide fragment does not inhibit at least one of the binding between the fusion polypeptides and the binding between the fusion polypeptide and the human-derived ferritin monomer.

12. A ferritin protein, comprising the fusion polypeptide of claim 1.

13. A polynucleotide encoding the fusion polypeptide of claim 1.

14. An expression vector, comprising the polynucleotide of claim 13.

15. A transforming method, the method comprising transforming a transformant with the expression vector of claim 14.

16. A protein cage comprising the fusion polypeptide of claim 1.

17. The fusion polypeptide of claim 1, wherein the fusion polypeptide specifically binds to a target material.

18. A drug delivery system comprising the fusion polypeptide of claim 1 as an active ingredient.

19. The drug delivery system of claim 18, wherein the drug delivery system specifically targets interleukin-4 receptor.

20. The drug delivery system of claim 18, wherein the fusion polypeptide comprises an amino acid sequence selected from the group consisting of SEQ ID NOs: 2-5, 23, 25, 27, 29, and 31.

21. A pharmaceutical composition, comprising the fusion polypeptide of claim 1 as an active ingredient for targeting and binding the interleukin-4-receptor.

22. The composition of claim 21, wherein the fusion polypeptide comprises an amino acid sequence selected from the group consisting of SEQ ID NOs: 2-5, 23, 25, 27, 29, and 31.

23. The composition of claim 21, for use in treating an interleukin-4-mediated disease selected from the group consisting of allergy, arteriosclerosis, and asthma.

24. A method for treating an interleukin-4-mediated disease, the method comprising administering the fusion polypeptide of claim 1 to a subject in need thereof,
wherein the disease is selected from the group consisting of allergy, arteriosclerosis, and asthma.

25. A method of manufacture, the method comprising preparing an agent for treating an interleukin-4-mediated disease by adding the fusion polypeptide of claim 1 to a pharmaceutically acceptable carrier.

26. An agent comprising, a fusion polypeptide that comprises an amino acid sequence selected from the group consisting of SEQ ID NOs: 2-5, 23, 25, 27, 29, and 31,
wherein the fusion polypeptide is an active ingredient for treating asthma.

* * * * *

SEQUENCE LISTING

<160> NUMBER OF SEQ ID NOS: 34

<210> SEQ ID NO 1
<211> LENGTH: 175
<212> TYPE: PRT
<213> ORGANISM: Homo Sapiens

<400> SEQUENCE: 1

Met Ser Ser Gln Ile Arg Gln Asn Tyr Ser Thr Asp Val Glu Ala Ala
 1               5                  10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

```
Ser His Phe Phe Arg Glu Leu Ala Glu Glu Lys Arg Glu Gly Tyr Glu
         50                  55                  60

Arg Leu Leu Lys Met Gln Asn Gln Arg Gly Gly Arg Ala Leu Phe Gln
 65                  70                  75                  80

Asp Ile Lys Lys Pro Ala Glu Asp Glu Trp Gly Lys Thr Pro Asp Ala
                 85                  90                  95

Met Lys Ala Ala Met Ala Leu Glu Lys Lys Leu Asn Gln Ala Leu Leu
                100                 105                 110

Asp Leu His Ala Leu Gly Ser Ala Arg Thr Asp Pro His Leu Cys Asp
            115                 120                 125

Phe Leu Glu Thr His Phe Leu Asp Glu Glu Val Lys Leu Ile Lys Lys
        130                 135                 140

Met Gly Asp His Leu Thr Asn Leu His Arg Leu Gly Pro Glu Ala
145                 150                 155                 160

Gly Leu Gly Glu Tyr Leu Phe Glu Arg Leu Thr Leu Lys His Asp
                165                 170                 175
```

<210> SEQ ID NO 2
<211> LENGTH: 183
<212> TYPE: PRT
<213> ORGANISM: Artificial Sequence
<220> FEATURE:
<223> OTHER INFORMATION: modified human ferritin light chain
    (hFL-GG-AP1S)

<400> SEQUENCE: 2

```
Met Ser Ser Gln Ile Arg Gln Asn Tyr Ser Thr Asp Val Glu Ala Ala
  1               5                  10                  15

Val Asn Ser Leu Val Asn Leu Tyr Leu Gln Ala Ser Tyr Thr Tyr Leu
                 20                  25                  30

Ser Leu Gly Phe Tyr Phe Asp Arg Asp Asp Val Ala Leu Glu Gly Val
             35                  40                  45

Ser His Phe Phe Arg Glu Leu Ala Glu Glu Lys Arg Glu Gly Tyr Glu
         50                  55                  60

Arg Leu Leu Lys Met Gln Asn Gln Arg Gly Gly Arg Ala Leu Phe Gln
 65                  70                  75                  80

Asp Ile Lys Lys Pro Ala Glu Asp Glu Trp Gly Lys Thr Pro Asp Ala
                 85                  90                  95

Met Lys Ala Ala Met Ala Leu Glu Lys Lys Leu Asn Gln Ala Leu Leu
                100                 105                 110

Asp Leu His Ala Leu Gly Ser Ala Arg Thr Asp Pro His Leu Cys Asp
            115                 120                 125

Phe Leu Glu Thr His Phe Leu Asp Glu Glu Val Lys Leu Ile Lys Lys
        130                 135                 140

Met Gly Asp His Leu Thr Asn Leu His Arg Gly Ser Arg Lys Arg Leu
145                 150                 155                 160

Asp Arg Asn Gly Gly Pro Glu Ala Gly Leu Gly Glu Tyr Leu Phe Glu
                165                 170                 175

Arg Leu Thr Leu Lys His Asp
                180
```

<210> SEQ ID NO 3
<211> LENGTH: 185
<212> TYPE: PRT
<213> ORGANISM: Artificial Sequence
<220> FEATURE:
<223> OTHER INFORMATION: modified human ferritin light chain (hFL-GG-AP1L)

<400> SEQUENCE: 3

```
Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Gly Ser Cys Arg Lys Arg
145                 150                 155                 160

Leu Asp Arg Asn Cys Gly Gly Pro Glu Ala Gly Leu Gly Glu Tyr Leu
                165                 170                 175

Phe Glu Arg Leu Thr Leu Lys His Asp
            180                 185
```

<210> SEQ ID NO 4
<211> LENGTH: 183
<212> TYPE: PRT
<213> ORGANISM: Artificial Sequence
<220> FEATURE:
<223> OTHER INFORMATION: modified human ferritin light chain
      (hFL-GP-AP1S)

<400> SEQUENCE: 4

```
Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Ser Arg Lys Arg
```

```
                145                 150                 155                 160
Leu Asp Arg Asn Gly Pro Glu Ala Gly Leu Gly Glu Tyr Leu Phe Glu
                    165                 170                 175

Arg Leu Thr Leu Lys His Asp
            180

<210> SEQ ID NO 5
<211> LENGTH: 185
<212> TYPE: PRT
<213> ORGANISM: Artificial Sequence
<220> FEATURE:
<223> OTHER INFORMATION: modified human ferritin light chain
      (hFL-GP-AP1L)

<400> SEQUENCE: 5

Met Ser Ser Gln Ile Arg Gln Asn Tyr Ser Thr Asp Val Glu Ala Ala
  1               5                  10                  15

Val Asn Ser Leu Val Asn Leu Tyr Leu Gln Ala Ser Tyr Thr Tyr Leu
                 20                  25                  30

Ser Leu Gly Phe Tyr Phe Asp Arg Asp Asp Val Ala Leu Glu Gly Val
             35                  40                  45

Ser His Phe Phe Arg Glu Leu Ala Glu Glu Lys Arg Glu Gly Tyr Glu
     50                  55                  60

Arg Leu Leu Lys Met Gln Asn Gln Arg Gly Gly Arg Ala Leu Phe Gln
 65                  70                  75                  80

Asp Ile Lys Lys Pro Ala Glu Asp Glu Trp Gly Lys Thr Pro Asp Ala
                 85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Ser Cys Arg Lys
145                 150                 155                 160

Arg Leu Asp Arg Asn Cys Gly Pro Glu Ala Gly Leu Gly Glu Tyr Leu
                165                 170                 175

Phe Glu Arg Leu Thr Leu Lys His Asp
            180                 185

<210> SEQ ID NO 6
<211> LENGTH: 7
<212> TYPE: PRT
<213> ORGANISM: Artificial Sequence
<220> FEATURE:
<223> OTHER INFORMATION: AP1S

<400> SEQUENCE: 6

Arg Lys Arg Leu Asp Arg Asn
  1               5

<210> SEQ ID NO 7
<211> LENGTH: 9
<212> TYPE: PRT
<213> ORGANISM: Artificial Sequence
<220> FEATURE:
<223> OTHER INFORMATION: AP1L

<400> SEQUENCE: 7

Cys Arg Lys Arg Leu Asp Arg Asn Cys
```

<210> SEQ ID NO 8
<211> LENGTH: 528
<212> TYPE: DNA
<213> ORGANISM: Homo Sapiens

<400> SEQUENCE: 8

| atgagctccc agattcgtca gaattattcc accgacgtgg aggcagccgt caacagcctg | 60 |
| gtcaatttgt acctgcaggc ctcctacacc tacctctctc tgggcttcta tttcgaccgc | 120 |
| gatgatgtgg ctctggaagg cgtgagccac ttcttccgcg aattggccga ggagaagcgc | 180 |
| gagggctacg agcgtctcct gaagatgcaa aaccagcgtg gcggccgcgc tctcttccag | 240 |
| gacatcaaga agccagctga agatgagtgg ggtaaaaccc cagacgccat gaaagctgcc | 300 |
| atggccctgg agaaaaagct gaaccaggcc ttttggatc ttcatgccct gggttctgcc | 360 |
| cgcacggacc cccatctctg tgacttcctg gagactcact tcctagatga ggaagtgaag | 420 |
| cttatcaaga gatgggtga ccacctgacc aacctccaca ggctgggtgg cccggaggct | 480 |
| gggctgggcg agtatctctt cgaaaggctc actctcaagc acgactaa | 528 |

<210> SEQ ID NO 9
<211> LENGTH: 552
<212> TYPE: DNA
<213> ORGANISM: Artificial Sequence
<220> FEATURE:
<223> OTHER INFORMATION: modified Human ferritin light chain
      (hFL-GG-AP1S)

<400> SEQUENCE: 9

| atgagctccc agattcgtca gaattattcc accgacgtgg aggcagccgt caacagcctg | 60 |
| gtcaatttgt acctgcaggc ctcctacacc tacctctctc tgggcttcta tttcgaccgc | 120 |
| gatgatgtgg ctctggaagg cgtgagccac ttcttccgcg aattggccga ggagaagcgc | 180 |
| gagggctacg agcgtctcct gaagatgcaa aaccagcgtg gcggccgcgc tctcttccag | 240 |
| gacatcaaga agccagctga agatgagtgg ggtaaaaccc cagacgccat gaaagctgcc | 300 |
| atggccctgg agaaaaagct gaaccaggcc ttttggatc ttcatgccct gggttctgcc | 360 |
| cgcacggacc cccatctctg tgacttcctg gagactcact tcctagatga ggaagtgaag | 420 |
| cttatcaaga gatgggtga ccacctgacc aacctccaca ggggatcccg taagcgtctt | 480 |
| gatcggaatg gtgggcccga ggctgggctg gcgagtatc tcttcgaaag gctcactctc | 540 |
| aagcacgact aa | 552 |

<210> SEQ ID NO 10
<211> LENGTH: 558
<212> TYPE: DNA
<213> ORGANISM: Artificial Sequence
<220> FEATURE:
<223> OTHER INFORMATION: modified Human ferritin light chain
      (hFL-GG-AP1L)

<400> SEQUENCE: 10

| atgagctccc agattcgtca gaattattcc accgacgtgg aggcagccgt caacagcctg | 60 |
| gtcaatttgt acctgcaggc ctcctacacc tacctctctc tgggcttcta tttcgaccgc | 120 |
| gatgatgtgg ctctggaagg cgtgagccac ttcttccgcg aattggccga ggagaagcgc | 180 |
| gagggctacg agcgtctcct gaagatgcaa aaccagcgtg gcggccgcgc tctcttccag | 240 |
| gacatcaaga agccagctga agatgagtgg ggtaaaaccc cagacgccat gaaagctgcc | 300 |

```
atggccctgg agaaaaagct gaaccaggcc cttttggatc ttcatgccct gggttctgcc      360
cgcacggacc cccatctctg tgacttcctg gagactcact tcctagatga ggaagtgaag      420
cttatcaaga agatgggtga ccacctgacc aacctccaca ggggatcctg ccgtaagcgt      480
cttgatcgga attgcggtgg gcccgaggct gggctgggcg agtatctctt cgaaaggctc      540
actctcaagc acgactaa                                                   558
```

```
<210> SEQ ID NO 11
<211> LENGTH: 552
<212> TYPE: DNA
<213> ORGANISM: Artificial Sequence
<220> FEATURE:
<223> OTHER INFORMATION: modified Human ferritin light chain
      (hFL-GP-AP1S)

<400> SEQUENCE: 11
```

```
atgagctccc agattcgtca gaattattcc accgacgtgg aggcagccgt caacagcctg       60
gtcaatttgt acctgcaggc ctcctacacc tacctctctc tgggcttcta tttcgaccgc      120
gatgatgtgg ctctggaagg cgtgagccac ttcttccgcg aattggccga ggagaagcgc      180
gagggctacg agcgtctcct gaagatgcaa aaccagcgtg gcggccgcgc tctcttccag      240
gacatcaaga agccagctga agatgagtgg ggtaaaaccc cagacgccat gaaagctgcc      300
atggccctgg agaaaaagct gaaccaggcc cttttggatc ttcatgccct gggttctgcc      360
cgcacggacc cccatctctg tgacttcctg gagactcact tcctagatga ggaagtgaag      420
cttatcaaga agatgggtga ccacctgacc aacctccaca ggctgggatc ccgtaagcgt      480
cttgatcgga atgggcccga ggctgggctg gcgagtatc tcttcgaaag gctcactctc      540
aagcacgact aa                                                         552
```

```
<210> SEQ ID NO 12
<211> LENGTH: 558
<212> TYPE: DNA
<213> ORGANISM: Artificial Sequence
<220> FEATURE:
<223> OTHER INFORMATION: modified Human ferritin light chain
      (hFL-GP-AP1L)

<400> SEQUENCE: 12
```

```
atgagctccc agattcgtca gaattattcc accgacgtgg aggcagccgt caacagcctg       60
gtcaatttgt acctgcaggc ctcctacacc tacctctctc tgggcttcta tttcgaccgc      120
gatgatgtgg ctctggaagg cgtgagccac ttcttccgcg aattggccga ggagaagcgc      180
gagggctacg agcgtctcct gaagatgcaa aaccagcgtg gcggccgcgc tctcttccag      240
gacatcaaga agccagctga agatgagtgg ggtaaaaccc cagacgccat gaaagctgcc      300
atggccctgg agaaaaagct gaaccaggcc cttttggatc ttcatgccct gggttctgcc      360
cgcacggacc cccatctctg tgacttcctg gagactcact tcctagatga ggaagtgaag      420
cttatcaaga agatgggtga ccacctgacc aacctccaca ggctgggatc ctgccgtaag      480
cgtcttgatc ggaattgcgg gcccgaggct gggctgggcg agtatctctt cgaaaggctc      540
actctcaagc acgactaa                                                   558
```

```
<210> SEQ ID NO 13
<211> LENGTH: 34
<212> TYPE: DNA
<213> ORGANISM: Artificial Sequence
<220> FEATURE:
```

<223> OTHER INFORMATION: Forward primer for GG-AP1S

<400> SEQUENCE: 13
gatcccgtaa gcgtcttgat cggaatggtg ggcc                                34

<210> SEQ ID NO 14
<211> LENGTH: 26
<212> TYPE: DNA
<213> ORGANISM: Artificial Sequence
<220> FEATURE:
<223> OTHER INFORMATION: Reverse primer for GG-AP1S

<400> SEQUENCE: 14
caccattccg atcaagacgc ttacgg                                         26

<210> SEQ ID NO 15
<211> LENGTH: 40
<212> TYPE: DNA
<213> ORGANISM: Artificial Sequence
<220> FEATURE:
<223> OTHER INFORMATION: Forward primer for GG-AP1L

<400> SEQUENCE: 15
gatcctgccg taagcgtctt gatcggaatt gcggtgggcc                          40

<210> SEQ ID NO 16
<211> LENGTH: 32
<212> TYPE: DNA
<213> ORGANISM: Artificial Sequence
<220> FEATURE:
<223> OTHER INFORMATION: Reverse primer for GG-AP1L

<400> SEQUENCE: 16
caccgcaatt ccgatcaaga cgcttacggc ag                                  32

<210> SEQ ID NO 17
<211> LENGTH: 31
<212> TYPE: DNA
<213> ORGANISM: Artificial Sequence
<220> FEATURE:
<223> OTHER INFORMATION: Forward primer for GP-AP1S

<400> SEQUENCE: 17
gatcccgtaa gcgtcttgat cggaatgggc c                                   31

<210> SEQ ID NO 18
<211> LENGTH: 23
<212> TYPE: DNA
<213> ORGANISM: Artificial Sequence
<220> FEATURE:
<223> OTHER INFORMATION: Reverse primer for GP-AP1S

<400> SEQUENCE: 18
cattccgatc aagacgctta cgg                                            23

<210> SEQ ID NO 19
<211> LENGTH: 37
<212> TYPE: DNA
<213> ORGANISM: Artificial Sequence
<220> FEATURE:
<223> OTHER INFORMATION: Forward primer for GP-AP1L

<400> SEQUENCE: 19
gatcctgccg taagcgtctt gatcggaatt gcgggcc                             37

<210> SEQ ID NO 20
<211> LENGTH: 29
<212> TYPE: DNA
<213> ORGANISM: Artificial Sequence
<220> FEATURE:
<223> OTHER INFORMATION: Reverse primer for GP-AP1L

<400> SEQUENCE: 20
cgcaattccg atcaagacgc ttacggcag                                29

<210> SEQ ID NO 21
<211> LENGTH: 66
<212> TYPE: DNA
<213> ORGANISM: Artificial Sequence
<220> FEATURE:
<223> OTHER INFORMATION: forward primers for FTL_AP1_AP1

<400> SEQUENCE: 21
gggcatatgc gtaagcgtct tgatcggaat ggaggaggaa gtggaatgag ctcccagatt    60
cgtcag                                                               66

<210> SEQ ID NO 22
<211> LENGTH: 29
<212> TYPE: DNA
<213> ORGANISM: Artificial Sequence
<220> FEATURE:
<223> OTHER INFORMATION: reverse primers for FTL_AP1_AP1

<400> SEQUENCE: 22
gctcgagtta gtcgtgcttg agagtgagc                                29

<210> SEQ ID NO 23
<211> LENGTH: 196
<212> TYPE: PRT
<213> ORGANISM: Artificial Sequence
<220> FEATURE:
<223> OTHER INFORMATION: FTL_AP1_AP1

<400> SEQUENCE: 23

Met Arg Lys Arg Leu Asp Arg Asn Gly Gly Gly Ser Gly Met Ser Ser
 1               5                  10                  15

Gln Ile Arg Gln Asn Tyr Ser Thr Asp Val Glu Ala Ala Val Asn Ser
            20                  25                  30

Leu Val Asn Leu Tyr Leu Gln Ala Ser Tyr Thr Tyr Leu Ser Leu Gly
         35                  40                  45

Phe Tyr Phe Asp Arg Asp Asp Val Ala Leu Glu Gly Val Ser His Phe
     50                  55                  60

Phe Arg Glu Leu Ala Glu Glu Lys Arg Glu Gly Tyr Glu Arg Leu Leu
 65                  70                  75                  80

Lys Met Gln Asn Gln Arg Gly Gly Arg Ala Leu Phe Gln Asp Ile Lys
                85                  90                  95

Lys Pro Ala Glu Asp Glu Trp Gly Lys Thr Pro Asp Ala Met Lys Ala
            100                 105                 110

Ala Met Ala Leu Glu Lys Lys Leu Asn Gln Ala Leu Leu Asp Leu His
         115                 120                 125

Ala Leu Gly Ser Ala Arg Thr Asp Pro His Leu Cys Asp Phe Leu Glu
     130                 135                 140

Thr His Phe Leu Asp Glu Glu Val Lys Leu Ile Lys Lys Met Gly Asp
145                 150                 155                 160

His Leu Thr Asn Leu His Arg Gly Ser Arg Lys Arg Leu Asp Arg Asn
                165                 170                 175

Gly Gly Pro Glu Ala Gly Leu Gly Glu Tyr Leu Phe Glu Arg Leu Thr
            180                 185                 190

Leu Lys His Asp
    195

<210> SEQ ID NO 24
<211> LENGTH: 591
<212> TYPE: DNA
<213> ORGANISM: Artificial Sequence
<220> FEATURE:
<223> OTHER INFORMATION: FTL_AP1_AP1

<400> SEQUENCE: 24
atgcgtaagc gtcttgatcg gaatggagga ggaagtggaa tgagctccca gattcgtcag      60
aattattcca ccgacgtgga ggcagccgtc aacagcctgg tcaatttgta cctgcaggcc     120
tcctacacct acctctctct gggcttctat ttcgaccgcg atgatgtggc tctggaaggc     180
gtgagccact tcttccgcga attggccgag gagaagcgcg agggctacga gcgtctcctg     240
aagatgcaaa accagcgtgg cggccgcgct ctcttccagg acatcaagaa gccagctgaa     300
gatgagtggg gtaaaacccc agacgccatg aaagctgcca tggccctgga gaaaaagctg     360
aaccaggccc tttttggatct tcatgccctg ggttctgccc gcacggaccc ccatctctgt     420
gacttcctgg agactcactt cctagatgag gaagtgaagc ttatcaagaa gatgggtgac     480
cacctgacca acctccacag gggatcccgt aagcgtcttg atcggaatgg tgggcccgag     540
gctgggctgg gcgagtatct cttcgaaagg ctcactctca agcacgacta a              591

<210> SEQ ID NO 25
<211> LENGTH: 192
<212> TYPE: PRT
<213> ORGANISM: Artificial Sequence
<220> FEATURE:
<223> OTHER INFORMATION: FTL_RGD_AP1

<400> SEQUENCE: 25

Met Arg Gly Asp Gly Gly Ser Gly Met Ser Ser Gln Ile Arg Gln
  1               5                  10                  15

Asn Tyr Ser Thr Asp Val Glu Ala Ala Val Asn Ser Leu Val Asn Leu
            20                  25                  30

Tyr Leu Gln Ala Ser Tyr Thr Tyr Leu Ser Leu Gly Phe Tyr Phe Asp
        35                  40                  45

Arg Asp Asp Val Ala Leu Glu Gly Val Ser His Phe Phe Arg Glu Leu
    50                  55                  60

Ala Glu Glu Lys Arg Glu Gly Tyr Glu Arg Leu Leu Lys Met Gln Asn
 65                  70                  75                  80

Gln Arg Gly Gly Arg Ala Leu Phe Gln Asp Ile Lys Lys Pro Ala Glu
                85                  90                  95

Asp Glu Trp Gly Lys Thr Pro Asp Ala Met Lys Ala Ala Met Ala Leu
           100                 105                 110

Glu Lys Lys Leu Asn Gln Ala Leu Leu Asp Leu His Ala Leu Gly Ser
        115                 120                 125

Ala Arg Thr Asp Pro His Leu Cys Asp Phe Leu Glu Thr His Phe Leu
    130                 135                 140

Asp Glu Glu Val Lys Leu Ile Lys Lys Met Gly Asp His Leu Thr Asn
145                 150                 155                 160

Leu His Arg Gly Ser Arg Lys Arg Leu Asp Arg Asn Gly Gly Pro Glu
                165                 170                 175

Ala Gly Leu Gly Glu Tyr Leu Phe Glu Arg Leu Thr Leu Lys His Asp
            180                 185                 190

<210> SEQ ID NO 26
<211> LENGTH: 579
<212> TYPE: DNA
<213> ORGANISM: Artificial Sequence
<220> FEATURE:
<223> OTHER INFORMATION: FTL_RGD_AP1

<400> SEQUENCE: 26
atgagaggtg atggaggagg aagtggaatg agctcccaga ttcgtcagaa ttattccacc    60
gacgtggagg cagccgtcaa cagcctggtc aatttgtacc tgcaggcctc ctacacctac   120
ctctctctgg gcttctattt cgaccgcgat gatgtggctc tggaaggcgt gagccacttc   180
ttccgcgaat tggccgagga aagcgcgag ggctacgagc gtctcctgaa gatgcaaaac   240
cagcgtggcg gccgcgctct cttccaggac atcaagaagc cagctgaaga tgagtggggt   300
aaaaccccag acgccatgaa agctgccatg gccctggaga aaaagctgaa ccaggccctt   360
ttggatcttc atgccctggg ttctgcccgc acggaccccc atctctgtga cttcctggag   420
actcacttcc tagatgagga agtgaagctt atcaagaaga tgggtgacca cctgaccaac   480
ctccacaggg gatcccgtaa gcgtcttgat cggaatggtg ggcccgaggc tgggctgggc   540
gagtatctct cgaaaggct cactctcaag cacgactaa                          579

<210> SEQ ID NO 27
<211> LENGTH: 195
<212> TYPE: PRT
<213> ORGANISM: Artificial Sequence
<220> FEATURE:
<223> OTHER INFORMATION: FTL_GRGDSP_AP1

<400> SEQUENCE: 27

Met Gly Arg Gly Asp Ser Pro Gly Gly Ser Gly Met Ser Ser Gln
  1               5                  10                  15

Ile Arg Gln Asn Tyr Ser Thr Asp Val Glu Ala Ala Val Asn Ser Leu
            20                  25                  30

Val Asn Leu Tyr Leu Gln Ala Ser Tyr Thr Tyr Leu Ser Leu Gly Phe
        35                  40                  45

Tyr Phe Asp Arg Asp Asp Val Ala Leu Glu Gly Val Ser His Phe Phe
    50                  55                  60

Arg Glu Leu Ala Glu Glu Lys Arg Glu Gly Tyr Glu Arg Leu Leu Lys
65                  70                  75                  80

Met Gln Asn Gln Arg Gly Gly Arg Ala Leu Phe Gln Asp Ile Lys Lys
                85                  90                  95

Pro Ala Glu Asp Glu Trp Gly Lys Thr Pro Asp Ala Met Lys Ala Ala
            100                 105                 110

Met Ala Leu Glu Lys Lys Leu Asn Gln Ala Leu Leu Asp Leu His Ala
        115                 120                 125

Leu Gly Ser Ala Arg Thr Asp Pro His Leu Cys Asp Phe Leu Glu Thr
    130                 135                 140

His Phe Leu Asp Glu Glu Val Lys Leu Ile Lys Lys Met Gly Asp His
145                 150                 155                 160

Leu Thr Asn Leu His Arg Gly Ser Arg Lys Arg Leu Asp Arg Asn Gly
                165                 170                 175

Gly Pro Glu Ala Gly Leu Gly Glu Tyr Leu Phe Glu Arg Leu Thr Leu
            180                 185                 190

Lys His Asp
        195

<210> SEQ ID NO 28
<211> LENGTH: 588
<212> TYPE: DNA
<213> ORGANISM: Artificial Sequence
<220> FEATURE:
<223> OTHER INFORMATION: FTL_GRGDSP_AP1

<400> SEQUENCE: 28

```
atgggaagag gtgattctcc aggaggagga agtggaatga gctcccagat tcgtcagaat    60
tattccaccg acgtggaggc agccgtcaac agcctggtca atttgtacct gcaggcctcc   120
tacacctacc tctctctggg cttctatttc gaccgcgatg atgtggctct ggaaggcgtg   180
agccacttct ccgcgaatt ggccgaggag aagcgcgagg gctacgagcg tctcctgaag   240
atgcaaaacc agcgtggcgg ccgcgctctc ttccaggaca tcaagaagcc agctgaagat   300
gagtggggta aaccccaga cgccatgaaa gctgccatgg ccctggagaa aaagctgaac   360
caggcccttt tggatcttca tgccctgggt tctgcccgca cggaccccca tctctgtgac   420
ttcctggaga ctcacttcct agatgaggaa gtgaagctta tcaagaagat gggtgaccac   480
ctgaccaacc tccacagggg atcccgtaag cgtcttgatc ggaatggtgg gcccgaggct   540
gggctgggcg agtatctctt cgaaaggctc actctcaagc acgactaa              588
```

<210> SEQ ID NO 29
<211> LENGTH: 192
<212> TYPE: PRT
<213> ORGANISM: Artificial Sequence
<220> FEATURE:
<223> OTHER INFORMATION: FTL_AP1_RGD

<400> SEQUENCE: 29

Met Arg Lys Arg Leu Asp Arg Asn Gly Gly Gly Ser Gly Met Ser Ser
 1               5                  10                  15

Gln Ile Arg Gln Asn Tyr Ser Thr Asp Val Glu Ala Ala Val Asn Ser
             20                  25                  30

Leu Val Asn Leu Tyr Leu Gln Ala Ser Tyr Thr Tyr Leu Ser Leu Gly
         35                  40                  45

Phe Tyr Phe Asp Arg Asp Asp Val Ala Leu Glu Gly Val Ser His Phe
     50                  55                  60

Phe Arg Glu Leu Ala Glu Glu Lys Arg Glu Gly Tyr Glu Arg Leu Leu
 65                  70                  75                  80

Lys Met Gln Asn Gln Arg Gly Gly Arg Ala Leu Phe Gln Asp Ile Lys
                 85                  90                  95

Lys Pro Ala Glu Asp Glu Trp Gly Lys Thr Pro Asp Ala Met Lys Ala
            100                 105                 110

Ala Met Ala Leu Glu Lys Lys Leu Asn Gln Ala Leu Leu Asp Leu His
        115                 120                 125

Ala Leu Gly Ser Ala Arg Thr Asp Pro His Leu Cys Asp Phe Leu Glu
    130                 135                 140

Thr His Phe Leu Asp Glu Glu Val Lys Leu Ile Lys Lys Met Gly Asp
145                 150                 155                 160

His Leu Thr Asn Leu His Arg Gly Ser Arg Gly Asp Gly Pro Glu
                165                 170                 175

Ala Gly Leu Gly Glu Tyr Leu Phe Glu Arg Leu Thr Leu Lys His Asp
            180                 185                 190

<210> SEQ ID NO 30
<211> LENGTH: 579
<212> TYPE: DNA
<213> ORGANISM: Artificial Sequence
<220> FEATURE:
<223> OTHER INFORMATION: FTL_AP1_RGD

<400> SEQUENCE: 30

```
atgcgtaagc gtcttgatcg gaatggagga ggaagtggaa tgagctccca gattcgtcag      60
aattattcca ccgacgtgga ggcagccgtc aacagcctgg tcaatttgta cctgcaggcc     120
tcctacacct acctctctct gggcttctat ttcgaccgcg atgatgtggc tctggaaggc     180
gtgagccact tcttccgcga attggccgag gagaagcgcg agggctacga gcgtctcctg     240
aagatgcaaa accagcgtgg cggccgcgct ctcttccagg acatcaagaa gccagctgaa     300
gatgagtggg gtaaaacccc agacgccatg aaagctgcca tggccctgga gaaaaagctg     360
aaccaggccc ttttggatct tcatgccctg ggttctgccc gcacggaccc ccatctctgt     420
gacttcctgg agactcactt cctagatgag gaagtgaagc ttatcaagaa gatgggtgac     480
cacctgacca acctccacag gggatccaga ggtgatggtg gcccgaggc tgggctgggc     540
gagtatctct tcgaaaggct cactctcaag cacgactaa                            579
```

<210> SEQ ID NO 31
<211> LENGTH: 195
<212> TYPE: PRT
<213> ORGANISM: Artificial Sequence
<220> FEATURE:
<223> OTHER INFORMATION: FTL_AP1_GRGDSP

<400> SEQUENCE: 31

```
Met Arg Lys Arg Leu Asp Arg Asn Gly Gly Gly Ser Gly Met Ser Ser
  1               5                  10                  15
Gln Ile Arg Gln Asn Tyr Ser Thr Asp Val Glu Ala Ala Val Asn Ser
             20                  25                  30
Leu Val Asn Leu Tyr Leu Gln Ala Ser Tyr Thr Tyr Leu Ser Leu Gly
         35                  40                  45
Phe Tyr Phe Asp Arg Asp Asp Val Ala Leu Glu Gly Val Ser His Phe
     50                  55                  60
Phe Arg Glu Leu Ala Glu Glu Lys Arg Glu Gly Tyr Glu Arg Leu Leu
 65                  70                  75                  80
Lys Met Gln Asn Gln Arg Gly Gly Arg Ala Leu Phe Gln Asp Ile Lys
                 85                  90                  95
Lys Pro Ala Glu Asp Glu Trp Gly Lys Thr Pro Asp Ala Met Lys Ala
            100                 105                 110
Ala Met Ala Leu Glu Lys Lys Leu Asn Gln Ala Leu Leu Asp Leu His
        115                 120                 125
Ala Leu Gly Ser Ala Arg Thr Asp Pro His Leu Cys Asp Phe Leu Glu
    130                 135                 140
Thr His Phe Leu Asp Glu Glu Val Lys Leu Ile Lys Lys Met Gly Asp
145                 150                 155                 160
His Leu Thr Asn Leu His Arg Gly Ser Gly Arg Gly Asp Ser Pro Gly
                165                 170                 175
Gly Pro Glu Ala Gly Leu Gly Glu Tyr Leu Phe Glu Arg Leu Thr Leu
            180                 185                 190
Lys His Asp
        195
```

```
<210> SEQ ID NO 32
<211> LENGTH: 588
<212> TYPE: DNA
<213> ORGANISM: Artificial Sequence
<220> FEATURE:
<223> OTHER INFORMATION: FTL_AP1_GRGDSP

<400> SEQUENCE: 32
atgcgtaagc gtcttgatcg gaatggagga ggaagtggaa tgagctccca gattcgtcag      60
aattattcca ccgacgtgga ggcagccgtc aacagcctgg tcaatttgta cctgcaggcc     120
tcctacacct acctctctct gggcttctat ttcgaccgcg atgatgtggc tctgaaggc      180 gtgagccact tcttccgcga attggccgag gagaagcgcg agggctacga gcgtctcctg     240
aagatgcaaa accagcgtgg cggccgcgct ctcttccagg acatcaagaa gccagctgaa     300
gatgagtggg gtaaaacccc agacgccatg aaagctgcca tggccctgga gaaaaagctg     360
aaccaggccc ttttggatct tcatgccctg ggttctgccc gcacggaccc ccatctctgt     420
gacttcctgg agactcactt cctagatgag gaagtgaagc ttatcaagaa gatgggtgac     480
cacctgacca acctccacag gggatccgga agaggtgatt ctccaggtgg gcccgaggct     540
gggctgggcg agtatctctt cgaaaggctc actctcaagc acgactaa                  588

<210> SEQ ID NO 33
<211> LENGTH: 3
<212> TYPE: PRT
<213> ORGANISM: Artificial Sequence
<220> FEATURE:
<223> OTHER INFORMATION: RGD

<400> SEQUENCE: 33

Arg Gly Asp
  1

<210> SEQ ID NO 34
<211> LENGTH: 6
<212> TYPE: PRT
<213> ORGANISM: Artificial Sequence
<220> FEATURE:
<223> OTHER INFORMATION: GRGDSP

<400> SEQUENCE: 34

Gly Arg Gly Asp Ser Pro
  1               5
```